(12) United States Patent
Kersbulck et al.

(10) Patent No.: US 11,447,836 B2
(45) Date of Patent: Sep. 20, 2022

(54) PROCESS FOR THE CONVERSION OF A SOLID MATERIAL CONTAINING HEMICELLULOSE, CELLULOSE AND LIGNIN

(71) Applicant: Avantium Knowledge Centre B.V., Amsterdam (NL)

(72) Inventors: Martijn Kersbulck, Amsterdam (NL); Benjamin McKay, Amsterdam (NL); Gerardus Johannes Maria Gruter, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 78 days.

(21) Appl. No.: 16/966,791

(22) PCT Filed: Jan. 31, 2019

(86) PCT No.: PCT/EP2019/052407
§ 371 (c)(1),
(2) Date: Jul. 31, 2020

(87) PCT Pub. No.: WO2019/149834
PCT Pub. Date: Aug. 8, 2019

(65) Prior Publication Data
US 2022/0081731 A1 Mar. 17, 2022

(30) Foreign Application Priority Data
Jan. 31, 2018 (NL) ..................................... 2020356

(51) Int. Cl.
*C13K 1/02* (2006.01)
*C13K 13/00* (2006.01)

(52) U.S. Cl.
CPC .............. *C13K 1/02* (2013.01); *C13K 13/002* (2013.01)

(58) Field of Classification Search
CPC .. C13K 1/02; C13K 13/002; B01D 2011/002; B01D 11/0219
See application file for complete search history.

(56) References Cited

U.S. PATENT DOCUMENTS 2,778,751 A 1/1957 Riehm
2,945,777 A 7/1960 Riehm
(Continued)

FOREIGN PATENT DOCUMENTS

WO 2016082816 A1 6/2016

OTHER PUBLICATIONS

Radillo et al., Fermentable Sugars From Lupinus rotundiflorus Biomass by Concentrated Hydrochloric Acid Hydrolysis, 2011, BioResources, vol. 6(1), pp. 344-355 (Year: 2011).*
(Continued)

*Primary Examiner* — Stefanie J Cohen
*Assistant Examiner* — Ritu S Shirali
(74) *Attorney, Agent, or Firm* — Suiter Swantz pc llo

(57) ABSTRACT

A process for obtaining aqueous hydrolysates from solid material containing hemicellulose, cellulose and lignin. The process comprises hydrolysing at least part of the hemicellulose of the solid material with a first aqueous hydrochloric acid solution at a concentration of 15-40 wt %, yielding a remaining solid material and an aqueous first hydrolysate product solution. The aqueous first hydrolysate is displaced from the remaining solid material with a non-aqueous displacement fluid having a density of less than 1000 kg/m³. Thereafter, at least part of the cellulose of the remaining solid material is hydrolysed with a second aqueous hydrochloric acid solution at a concentration of 40-51 wt %, yielding a residue and an aqueous second hydrolysate product solution. This process is carried out in vertical cylindrical reactors, and the displacement fluid is supplied to a reactor in a downward fashion.

14 Claims, 5 Drawing Sheets

(56) References Cited

U.S. PATENT DOCUMENTS

2009/0114591 A1* 5/2009 Holtzapple ............. C13B 10/04
210/612
2015/0167235 A1* 6/2015 Powell .................... C13K 1/02
568/861

OTHER PUBLICATIONS

Chen, Lignocellulose Biorefinery Feedstock Engineering, 2015, Principles and Applications, pp. 37-86 (Year: 2015).*
Engineering Tool Box : Liquids—Densities [online], [retrieved on Dec. 29, 2021], Retrieved from the internet < URL: https://www.engineeringtoolbox.com/liquids-densities-d_743.html> (Year: 2021).*
Engineering Tool Box: Liquids and Gases—Boiling Points [online], [retrieved on Dec. 15, 2021], Retrieved from the internet:< URL: https://www.engineeringtoolbox.com/boiling-points-fluids-gases-d_155.html> (Year: 2021).*
Cheric: Temperature Dependent Properties—Liquid Viscosity of Ethanol [online], [retrieved on Dec. 13, 2021], Retrieved from the internet: < URL: https://www.cheric.org/research/kdb/hcprop/showcoef.php?cmpid=818&prop=VSL> (Year: 2021).*
Machine translation of WO 2016/082816 A1 originally published Jun. 2016 to Kose et al. (Year: 2016).*
International Search Report and Written Opinion dated Jun. 3, 2019 for PCT/EP2019/052407.

* cited by examiner

PROCESS FOR THE CONVERSION OF A SOLID MATERIAL CONTAINING HEMICELLULOSE, CELLULOSE AND LIGNIN

FIELD OF THE INVENTION

The present invention relates to a process for the conversion of a solid material containing hemicellulose, cellulose and lignin, more specifically it relates to a process for the conversion of a solid lignocellulosic material.

BACKGROUND TO THE INVENTION

With the diminishing supply of crude petroleum oil, use of sustainable, renewable biomass materials are becoming increasingly important for the production of fuels and/or chemicals. Lignocellulosic materials, such as wood or agricultural waste, are suitable examples of such renewable biomass material. The production of fuels and/or chemicals from non-edible sustainable, renewable biomass materials, such as solid lignocellulosic material, is preferred, as such non-edible solid lignocellulosic material does not compete with food production.

Several processes have been examined to convert solid lignocellulosic materials such as wood or agricultural waste to saccharides, which saccharides in turn can conveniently be converted to fuels and/or chemicals. Quite a number of these processes involve the hydrolysis of solid lignocellulosic materials to produce saccharides. Examples of these hydrolysis methods include the Bergius Rheinau process.

In the Bergius Rheinau process solid lignocellulosic material, such as wood, is treated with at least one concentrated hydrochloric acid composition. During the treatment for instance about two-thirds of the wood may be dissolved by the hydrochloric acid in the form of mono- and oligosaccharides, and the remainder may remain as lignin. The dissolved fraction can comprise mono- and oligosaccharides, together with water and hydrochloric acid. This fraction is also referred to as the hydrolysate. The term "hydrolysate" is well known by persons skilled in the art to refer to any product(s) of hydrolysis.

The hydrolysis of the lignocellulosic material can also be conducted in two stages. In a first stage, a so-called pre-hydrolysis can be conducted, wherein the hemicellulose in the lignocellulosic material can be digested, yielding a mixture, also referred to as a pre-hydrolysate, comprising xylose, arabinose, mannose, glucose and their oligomers as saccharides. In a second stage a so-called main hydrolysis can be conducted, wherein the portion of the lignocellulosic material remaining after the pre-hydrolysis, consisting to a large extent of cellulose, can subsequently be digested with more concentrated HCl, yielding mainly glucose and its oligomers as saccharides in the hydrolysate.

Examples of the Bergius Rheinau process include the Bergius Rheinau process as amended by Riehm, as described in for example U.S. Pat. Nos. 2,945,777 and 2,778,751.

U.S. Pat. No. 2,945,777 describes a process for the saccharification of soft wood sawdust comprising a prehydrolysis step and a main hydrolysis step. In the first step the sawdust is subjected at a temperature of about 15 to 30° C. to a prehydrolysis with hydrochloric acid containing 34 to 37 percent of HCl by weight for a time sufficient to dissolve substantially the hemicelluloses in an amount corresponding to about 22 to 26 percent of the dry wood substance and the obtained solution is subsequently separated from the solid residue. In the second step the solid residue of said prehydrolysis is treated in a main hydrolysis with hydrochloric acid of about 40 to 42% HCl content and crystalline glucose is recovered from the sugar syrup obtained in said main hydrolysis. The process is exemplified in example 1 with a process in which pinewood sawdust is subjected to hydrolysis with 32% hydrochloric acid, after which the solution (hydrochloric acid with dissolved hydrolysed hemicellulose) is filtered (i.e. drained) off, and the wood residue is washed and dried. Subsequently, the main hydrolysis is carried out with 41% hydrochloric acid solution.

U.S. Pat. No. 2,778,751 also relates to a process for the hydrolysis of wood with concentrated hydrochloric acid. A characteristic of the process as disclosed by U.S. Pat. No. 2,778,751 is that it uses a lot of water, including wash acid which is dilute hydrochloric acid (0.5-3% HCl), next to the strong hydrochloric acid (41% HCl), as is clear from FIG. 1 and the description. The described process comprises providing a plurality of separate stationary columns of lignin-containing prehydrolyzed cellulosic material, said columns being connected in series to form a saccharification unit. The process includes introducing continuously concentrated hydrochloric acid containing about 40% by weight of HCl into said unit to hydrolyze the cellulose to sugar. A liquid column consisting of defined contiguous zones is caused to travel continuously through the stationary wood, and the zones of the traveling column are maintained stationary by providing the reaction towers with inlets and outlets through which the required liquids are introduced into suitable zones of the traveling liquid column and through which suitable amounts of liquid are withdrawn from other zones, respectively.

U.S. Pat. No. 2,778,751 dating back to 1957, indicates that in order to ensure an entirely uniform travel of the whole liquid column, wherein the concentration of the various zones remains constant, theoretically an infinite or at least a very large number of inlet and outlets should be provided. U.S. Pat. No. 2,778,751 optimistically indicates that it was found in practice that a relatively small number of such inlets and outlets is sufficient. It describes the intermittent advance of the acid flow being balanced by a layer of high concentrated substantially sugar-free hydrochloric acid between an acid sugar solution and a dilute acid, and the change of the direction of the flow from the foremost to the next succeeding tower being rendered innocuous by providing a sufficiently prolonged layer of a concentrated sugar solution containing, for instance about 20 to 25 grams of sugar per 100 $cm^3$ of solution.

More recent WO2016/082816, however, is less optimistic. WO2016/082816 describes how in a process comprising a first step, wherein 35 to 37% hydrochloric acid is slowly fed to a reactor with biomass, and a second step, wherein 40 to 42% hydrochloric acid is introduced through such reactor, the 40 to 42% hydrochloric acid displaces, on the basis of its density, the already present acid with a lower concentration. The flow rate is to be measured such that the displacement leads to a mere minimal mixing of the two acid fractions. WO2016/082816 further describes that also the acid is to be removed from the reactor and notes that the residue in the reactor (lignin) itself binds hydrochloric acid. The acid was displaced by introducing water slowly. Again, it was noted that the displacement with water was carried out so slowly that the mixing between the acid and water could be kept as low as possible. With the addition of water, also hydrochloric acid bound to the above mentioned lignin residue is said to be released. WO2016/082816 subsequently describes that residual hydrochloric acid could only be removed by applying large amounts of water, leading to a so-called "tail" in the concentration profile.

Recent US2015/0275320 also describes a process for the hydrolytic breakdown of plant biomass via hydrochloric acid. It describes a first phase starting with the slow introduction of the acid into the reactor and ending when the reactor is completely filled with acid. According to US2015/0275320 the solid residue has a lower density at this point than the surrounding liquid and a floating situation more or less comes about in the reactor. The described second phase starts with the introduction of water from above and the displacement of the acid according to the density principle. This means that there will ideally not be any mixture of the hydrolysate solution having a heavier specific weight with the water having a lighter specific weight when there is a correspondingly slower and more even introduction. US2015/0275320 warns that if introduction is too fast, that could lead to a situation in which the displacement is no longer uniform along the entire tube cross section.

From the above it becomes clear that the flow regime in a Bergius Rheinau process as amended by Riehm, as described in for example U.S. Pat. Nos. 2,945,777 and 2,778,751 is far from plug flow and substantial back mixing exists. This can be disadvantageous for several reasons.

Without excessive and costly washing, residual $C_5$-saccharides (also referred to as pentoses or $C_5$-sugars) from a pre-hydrolysis step can be carried over into a main hydrolysis step. This reduces the purity of a resulting product of the main hydrolysis step. Unlike the $C_6$-saccharides (also referred to as hexoses or $C_6$-sugars) obtained in the main hydrolysis step, pentoses are for example difficult to ferment. Also for chemical conversions, relatively pure $C_6$-saccharides are preferred rather than mixtures of $C_5$-saccharides and $C_6$-saccharides.

Secondly, hydrochloric acid can be carried over into the wash water used in a washing step and can only be removed from such washing water at great expense. Apart from hydrochloric acid being carried over into wash water, for any modified process it is preferred that the amount of water (or aqueous liquids other than the hydrochloric acids needed for hydrolysis of hemicellulose and cellulose) being used in hydrochloric acid-based hydrolysis of biomass containing cellulose, hemi-cellulose and lignin is kept to a minimum, as any such water will need to be collected, stored in tanks, and purified, as they are easily contaminated with a few percent of hydrochloric acid. As handling hydrochloric acid solutions has its requirements, it is preferred that the number of different hydrochloric acid solutions used is also kept to a minimum. If wash water is required, it is preferred that the mixing of wash water with pre-hydrolysate and hydrolysate is kept to a minimum, as such dilutes the product streams and leads to wash water contaminated with acids.

It would be an advancement in the art to provide a Bergius Rheinau process as described above wherein back-mixing can be substantially reduced and/or wherein the purity of the product of the main hydrolysis step can otherwise be improved and/or wherein the process can be carried out continuously or semi-continuously in a more efficient manner. It is also desired that process control should preferably be easy and straightforward, particularly on separating the hydrolysate of hemi-cellulose and the hydrolysate of cellulose as best as possible. Elements of such process control can be a minimum number of pumps that are required (put differently a low ratio pumps over number of reactors) and/or that the flow through the reactors resembles to a reasonable extent plug flow and/or the ability to keep the acid used for hydrolysis of hemi-cellulose as much as possible of the acid used for hydrolysis if cellulose, as such may facilitate recycling of the acids.

SUMMARY OF THE INVENTION

Such a process has been achieved with the process according to the invention. Accordingly the present invention provides a process for the conversion of a solid material containing hemicellulose, cellulose and lignin, which process comprises the following steps:

(i) hydrolyzing, at a temperature equal to or less than 40° C., preferably equal to or less than 30° C., at least part of the hemicellulose of the solid material by contacting the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution, yielding a remaining solid material and an aqueous first hydrolysate product solution;

(ii) displacing aqueous solution from the remaining solid material with a non-aqueous displacement fluid;

(iii) hydrolyzing, at a temperature equal to or less than 40° C., preferably equal to or less than 30° C., at least part of the cellulose of the remaining solid material by replacing the non-aqueous displacement fluid with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution, yielding a residue and an aqueous second hydrolysate product solution, wherein the process is carried out in one or more reactors and wherein the reactor comprises a cylindrical vessel with its axis arranged in an essentially vertical manner, and wherein said non-aqueous displacement fluid is a non-aqueous, preferably hydrophobic, liquid having a density equal to or less than 1000 kilograms per cubic meter (kg/m3), and wherein the non-aqueous displacement fluid is supplied to such reactor in a downward fashion.

The process according to the invention may optionally further comprise an additional step (iv) of displacing aqueous solution from the residue with additional non-aqueous displacement fluid.

The displacement with the non-aqueous displacement fluid has several advantages.

Due to the composition of the hemicellulose, hydrolyzing of the hemicellulose in step (i) may result in an aqueous first hydrolysate product solution containing a mixture of $C_5$-saccharides and $C_6$-saccharides and a remaining solid material comprising predominantly lignin and cellulose. The subsequent hydrolysis of the cellulose in the remaining solid material in step (iii) can subsequently result in an aqueous second hydrolysate product solution believed to predominantly comprise $C_6$ saccharides.

As explained above, back-mixing of $C_5$ saccharides from the first hydrolysate product solution into the second hydrolysate product solution is highly undesirable. The use of the non-aqueous displacement fluid(s) allows one to reduce back mixing of components of the first hydrolysate product solution into the second hydrolysate solution. By reducing the back mixing, contamination of the second hydrolysate product solution with $C_5$ saccharides can be reduced.

In addition, the non-aqueous displacement fluid can be used to compensate for volume losses during the process, which volume losses are due to the reduction of solid material volume. Compensation of such volume losses allows one to maintain a sufficient flowrate and to operate the process continuously or semi-continuously in a more efficient manner.

DETAILED DESCRIPTION OF THE INVENTION

Figure 1A:
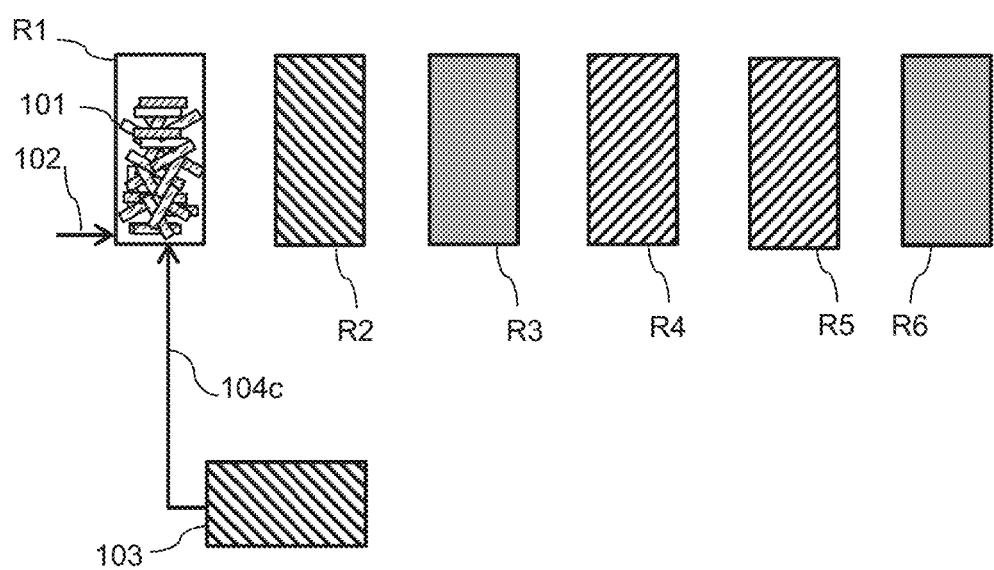
FIGS. 1A, 1B and 1C illustrate a first cycle, starting at a time "t", of a process according to the invention.

The present invention relates to a process for the conversion of a solid material containing hemicellulose, cellulose and lignin. Suitably such solid material is a solid lignocellulosic material.

By cellulose (also herein referred to as cellulosic material) is herein understood a homopolysaccharide comprising glucose-based monomer units, such as cellobiose.

Hemicellulose (also herein referred to as hemicellulosic material) is also a polysaccharide, but differs from cellulose. Hemicelluloses may for example comprise pentose monomer units, such as xylose and arabinose, hexose monomer units, such as glucose and mannose, hexuronic acid and deoxy-hexose based monomer units. Whereas some hemicelluloses may essentially consist of only one single type of monomer unit (for example xylans comprising essentially only xylose), most hemicelluloses may comprise several different types of monomer units (such as for example glucomannans comprising glucose and mannose).

The process according to the invention can use a wide variety of solid lignocellulosic materials as feedstock. Examples of solid lignocellulosic materials that may suitably be used in the process of the invention include for example agricultural wastes such as stover (for example corn stover and soybean stover), corn cobs, rice straw, rice hulls, oat hulls, corn fibre, cereal straws such as wheat, barley, rye and oat straw; grasses; forestry products and/or forestry residues such as wood and wood-related materials such as sawdust and bark; waste paper; sugar processing residues such as bagasse and beet pulp; or mixtures thereof. More preferably the solid lignocellulosic material is selected from the group consisting of wood, sawdust, bark, straw, hay, grasses, bagasse, corn stover and/or mixtures thereof.

Preferably the solid lignocellulosic material is non-edible, to prevent the process from being in competition with food-production. Most preferably the solid lignocellulosic material comprises or consists of wood. The wood may include soft wood and/or hard wood and may originate from all types of trees, including spruce, pine, willow, larch, oak, birch, poplar, eucalyptus and other trees.

The solid lignocellulosic material may conveniently be washed, dried, roasted, torrefied and/or reduced in particle size before it is used as a feedstock in the process according to the invention. The solid lignocellulosic material may conveniently be supplied or be present in a variety of forms, including chips, pellets, powder, chunks, briquettes, crushed particles, milled particles, ground particles or a combination of two or more of these. When the solid lignocellulosic material is wood, it can for example be supplied or be present in the form of wood powder, wood chips, wood pellets, wood briquettes, wood chunks or a combination of two or more of these.

When the solid lignocellulosic material is wood, such wood is most preferably supplied or present in the form of wood chips. When the solid lignocellulosic material comprises grass, bagasse and/or stover, such grass, bagasse and/or stover is most preferably supplied or present in the form of pellets. Such pellets advantageously provide unstructured biomass, such as grass, bagasse and/or stover, with a desired morphology. Such morphology can advantageously limit the collapse of the material inside the reactors upon hemicellulose and cellulose hydrolysis, which otherwise could result in an undesired pressure drop.

The process according to the invention can be a batch-wise, semi-continuous or continuous process. As explained below, the process according to the invention can further be carried out in one reactor or in a series of reactors.

The solid lignocellulosic material can be provided to a reactor, suitably in any manner known by the person skilled in the art. The solid lignocellulosic material can for example be provided to a reactor by means of a feed hopper, conveyer belt, screw feeder or a combination thereof. The solid lignocellulosic material may suitably be loaded into a reactor, for example in a batch-wise, semi-continuous or continuous manner. Preferably the solid lignocellulosic material is loaded into a reactor via one or more inlets located at the top of the reactor and/or via one or more lateral inlets located in the reactor wall.

Different types of reactor can be used. The process according to the invention can be carried out in any reactor known by the person skilled in the art to be suitable for a hydrolysis reaction. Such reactors are herein also referred to as "hydrolysis reactor(s)".

Preferably the process is carried out in one or more reactors as described for a Bergius Rheinau process. Preferably such a reactor comprises a cylindrical vessel with its axis arranged in an essentially vertical manner. Preferably the reactor is an essentially vertical, tubular reactor. If so desired, the reactor may be slightly tilted such as for example described in US20150275320. Preferably the reactor is conically tapered at the top and bottom. The ratio of diameter to height may suitably range from equal to or more than 1:10 (diameter:height) to equal to or less than 1:4 (diameter:height). The reactor can suitably be provided with a discharge opening that can be opened and closed, to allow for discharge of any residual lignin after the process. Preferably such a discharge opening is located at the bottom of such a reactor.

Examples of suitable reactors include the reactors as described in for example U.S. Pat. No. 2,778,751, EP1878480, WO2015/136044 and non-prepublished PCT/EP2017/071914. The aqueous hydrochloric acid solutions can advantageously flow through such hydrolysis reactors in an intermittent, continuous or semi-continuous manner.

Step (i) is preferably preceded by a loading step wherein solid lignocellulosic material is loaded into the reactor as described in more detail above.

Step (i) suitably comprises hydrolyzing, at a temperature equal to or less than 40° C., preferably equal to or less than 30° C., at least part of the hemicellulose of the solid material by contacting the solid material with a first aqueous hydrochloric acid solution, which first aqueous hydrochloric acid solution has a hydrochloric acid concentration in the range from equal to or more than 15.0 wt. % to less than 40.0 wt.

%, based on the weight amount of water and hydrochloric acid in such first aqueous hydrochloric acid solution. Such step (i) suitably yields an aqueous first hydrolysate product solution. In addition there will be remaining solid material. Such remaining solid material suitably still comprises cellulose and lignin. This remaining solid material can herein also be referred to as "pre-hydrolyzed solid material".

By hydrolyzing, respectively hydrolysis, is herein understood the breaking of bonds between saccharide units in a polysaccharide, such as hemicellulose or cellulose, to yield monosaccharides, disaccharides and/or oligosaccharides (by oligo-saccharides are herein understood saccharide chains comprising in the range from 3 to 10 mono-saccharide units). The product(s) of a hydrolysis are also referred to as "hydrolysate".

As explained above, the hydrolysis of hemicellulose is also known as "pre-hydrolysis" and the products of the hydrolysis of hemicellulose are also known as "pre-hydrolysate". Step (i) is therefore herein also referred to as "pre-hydrolysis" or "pre-hydrolyzing". The first hydrolysate product solution obtained by hydrolysis of the hemicellulose in step (i) is the first hydrolysate product solution obtained in the process. It can herein also be referred to as "pre-hydrolysate", "pre-hydrolysate solution" or "hemicellulose hydrolysate solution". As explained above, such first hydrolysate product solution can suitably contain a mixture of $C_5$-saccharides and $C_6$-saccharides. The first hydrolysate product solution can for example contain xylose, arabinose, mannose, glucose, their oligomers and mixtures thereof.

As illustrated by the hydrochloric acid concentration, the conditions for the pre-hydrolysis of step (i) are less severe than the conditions for the main hydrolysis of step (iii) described below. Under the conditions of step (i), hemicellulose can be selectively hydrolyzed. The hydrolyzing of the hemicellulose can already be effected by the mere contacting of the solid lignocellulosic material with the first aqueous hydrochloric acid solution.

An elevated temperature is not required. Step (i) can therefore conveniently be carried out at about ambient temperature (20° C.). For practical purposes step (i) is preferably carried out at a temperature equal to or more than 0° C. and preferably equal to or less than 30° C. It is believed that at temperatures higher than 30° C., cellulose may start to become hydrolyzed and hence selectivity towards hemicellulose hydrolysis may decrease. In addition, such hydrolysis of cellulose may lead to lower yields in step (iii).

Step (i) can be carried out over a wide range of pressures. Conveniently a pressure of about 0.1 MegaPascal (corresponding to about 1 bar) can be applied. All pressure herein are absolute pressures.

The hydrochloric acid concentration for first aqueous hydrochloric acid solution as indicated above is based on the weight amount of water and hydrochloric acid contained in the first aqueous hydrochloric acid solution. Preferably the first aqueous hydrochloric acid solution has a hydrochloric acid concentration in the range from equal to or more than 34.0 wt. % to equal to or less than 39.9 wt. %, more preferably in the range from in the range from equal to or more than 36.0 wt. % to equal to or less than 39.0 wt. %, based on the weight amount of water and hydrochloric acid contained in the first aqueous hydrochloric acid solution.

The combination of pressure, temperature and hydrochloric acid concentration can be optimized to achieve optimal selectivity in the hydrolysis of hemicellulose. Preferably a combination of pressure, temperature and hydrochloric acid concentration is applied such that the hydrochloric acid remains completely dissolved in the solution as hydrogen ions and chloride ions. More preferably the combination of pressure, temperature and hydrochloric acid concentration is such that no molecular hydrochloric acid remains in solution. Further guidance on this aspect can for example be found by plotting the boiling point of an aqueous hydrochloric acid solution as a function of the hydrochloric acid concentration at the applied pressure. The combination of pressure, temperature and hydrochloric acid concentration applied during step (i) is most preferably such that the boiling point is not exceeded.

For practical purposes it is preferred that, suitably at a pressure of about 0.1 MegaPascal, the result of multiplying the temperature (in ° C.) with the weight percentage (wt. %) hydrochloric acid concentration, based on the weight amount of water and hydrochloric acid contained in the first aqueous hydrochloric acid solution, is equal to or less than 1000. This is illustrated by formula (I) below $$\text{Temperature}(°\text{ C.}) \times \text{concentration}(\text{wt. \%}) \leq 1000 \quad (I)$$

During step (i) hemicellulose is being hydrolyzed and the resulting saccharides become dissolved in the first aqueous hydrochloric acid solution. Therefore, in addition to the water and the hydrochloric acid, the first aqueous hydrochloric acid solution may or may not contain other compounds such as for example dissolved saccharides.

When freshly added to the process, the first aqueous hydrochloric acid solution (also referred to as fresh first aqueous hydrochloric acid solution) preferably comprises only minor amounts or even essentially no dissolved saccharides.

After absorbing saccharides, the first aqueous hydrochloric acid solution is no longer fresh. Such a first aqueous hydrochloric acid solution that further contains dissolved saccharides is herein also referred to as "intermediate pre-hydrolysate solution" or as "intermediate pre-hydrolysate". The intermediate pre-hydrolysate solution can suitably contain saccharides (such as a mixture of $C_5$-saccharides and $C_6$-saccharides) dissolved in an aqueous hydrochloric acid solution. Such intermediate pre-hydrolysate solution may therefore also be referred to as an, hydrochloric acid-containing, aqueous intermediate pre-hydrolysate solution. The intermediate pre-hydrolysate solution may suitably still be used for contacting further, optionally partly pre-hydrolyzed, solid material to suitably absorb further saccharides therefrom.

To obtain the best results, the solid material is preferably soaked in first aqueous hydrochloric acid solution. Such first aqueous hydrochloric acid solution may or may not contain saccharides.

Step (i) suitably yields an aqueous first hydrolysate product solution and pre-hydrolyzed solid material. The first hydrolysate product solution is suitably an aqueous hydrolysate solution. As explained, one skilled in the art will understand that such solution suitably contains the products of the hydrolysis of the hemicellulose.

Without wishing to be bound by any kind of theory it is believed that during the pre-hydrolysis in step (i), predominantly any hemicellulose present in solid material can be hydrolyzed. This may suitably result in an aqueous first hydrolysate product solution that may comprise or consist of an aqueous solution containing hydrochloric acid and a mixture of mono- di- and oligo-saccharides of pentoses (i.e. $C_5$-saccharides, that is, sugars whose molecules contain five carbon atoms) and hexoses (i.e. $C_6$-saccharides, that is, sugars whose molecules contain six carbon atoms).

The first hydrolysate product solution may include for example pentose monosaccharides, hexose monosaccharides, pentose disaccharides, hexose disaccharides, and pentose-hexose disaccharides, pentose oligosaccharides, hexose oligosaccharides and/or oligosaccharides of mixtures of pentoses and hexoses. Suitably the first hydrolysate product solution can comprise one or more compounds selected from the group consisting of glucose, fructose, mannose, galactose, arabinose, xylose, sucrose, cellobiose, ribulose, ribose, lyxose, allose, altrose, glucose dimers (such as maltose), glucose trimers, cellotriose, maltotriose, cellodextrins, dextrins, xylan-oligosaccharides, mannan-oligosaccharides, arabinan-oligosaccharides and oligofructans. More suitably the first hydrolysate product solution can comprise at least one compound selected from the group consisting of mannose, glucose, galactose, arabinose and xylose or their dimers or oligomers.

Preferably the first hydrolysate product solution contains a total amount of saccharides (including mono-, di- and/or oligosaccharides) of equal to or more than 2 wt. % saccharides, more preferably of equal to or more than 5 wt. % saccharides, still more preferably of equal to or more than 10 wt. % saccharides, and most preferably of equal to or more than 20 wt. % saccharides, based on the total weight of the first hydrolysate product solution. The upper limit for the saccharide content in the first hydrolysate product solution is formed by the solubility of the saccharides in the solution. For practical purposes the first hydrolysate product solution may suitably contain a total amount of saccharides (including mono-, di- and/or oligosaccharides) of equal to or less than 45 wt. %, more preferably of equal to or less than 40 wt. % saccharides, based on the total weight of the first hydrolysate product solution.

In addition to the saccharides, the first hydrolysate product solution can suitably contain hydrochloric acid. Preferably, the first hydrolysate product solution can have a hydrochloric acid concentration in the range from equal to or more than 1.0 wt. % to equal to or less than 40.0 wt. %, more preferably in the range from equal to or more than 10.0 wt. % to equal to or less than 39.0 wt. %, based on the weight of the combination of hydrochloric acid and water.

The remaining solid material may suitably comprise predominantly lignin and cellulose. Preferably the remaining solid material contains mere minor amounts or essentially no hemicellulose. Preferably, the hemicellulose content of solid material used as a feedstock to the process has been reduced by at least at least 85 wt. %, more preferably at least 95 wt. %, and preferably essentially 100 wt. %. That is, preferably at least 85 wt. %, more preferably at least 95 wt. %, and most preferably essentially 100 wt. % of the hemicellulose in the solid material used as a feedstock is hydrolyzed in step (i). The remaining solid material may thus comprise equal to or less than 10 wt. %, more preferably equal to or less than 5 wt. %, most preferably equal to or less than 1 wt. % of the hemicellulose that was present in the solid material used as a feedstock. Most preferably the remaining solid material comprises essentially no hemicellulose.

Step (ii) suitably comprises displacing aqueous solution from the remaining solid material with a non-aqueous displacement fluid. Such displacing may suitably comprise contacting the remaining solid material with the non-aqueous displacement fluid. Preferably the non-aqueous displacement fluid displaces any hydrochloric acid—containing and/or saccharide-containing aqueous solution from the pre-hydrolyzed solid material. For example, the non-aqueous displacement fluid can suitably displace any first aqueous hydrochloric acid solution, any intermediate pre-hydrolysate solution and/or any first hydrolysate product solution from the pre-hydrolyzed solid material. By displacing is herein understood "taking over its place". Preferably, whenever in the process of the invention a preceding fluid is displaced by a succeeding fluid, the preceding fluid is forced from its location (such as for example its location in the solid material) and replaced by the succeeding fluid. Preferably this displacement is carried out such that at least 80 wt. %, more preferably at least 90 wt. %, even more preferably at least 95 wt. % and still more preferably 99 wt. % of the preceding fluid, based on the total weight of preceding fluid originally present, is displaced with the succeeding fluid. Most preferably essentially all or 100 wt. %, based on the total weight of preceding fluid originally present, of the preceding fluid is displaced with the succeeding fluid.

The aqueous solution that is being displaced can suitably be any aqueous first hydrochloric acid solution, any aqueous intermediate pre-hydrolysate solution, any aqueous first hydrolysate product solution and/or any other aqueous solution that is residing with and/or on the remaining solid material. In this manner any such aqueous solution(s) can suitably be separated from the remaining solid material (i.e. the pre-hydrolyzed solid material). Preferably, the non-aqueous displacement fluid is hydrophobic. Without wishing to be bound by any kind of theory, it is believed that the non-aqueous, preferably hydrophobic, displacement fluid can penetrate the remaining solid material and pushes first hydrolysate product solution that is being retained by such remaining solid material out of such pre-hydrolyzed solid material.

By a non-aqueous displacement fluid is herein preferably understood a fluid that preferably contains equal to or less than 1 kilograms per cubic meter ($kg/m^3$), more preferably equal to or less than 0.2 $kg/m^3$ and even more preferably equal to or less than 0.02 kilograms per cubic meter ($kg/m^3$) of water. Most preferably the non-aqueous displacement fluid is essentially water-free. Preferably the non-aqueous displacement fluid is essentially immiscible with water and/or an aqueous hydrochloric acid solution and/or an aqueous first hydrolysate product solution and/or an aqueous second hydrolysate product solution as described herein.

Preferably the non-aqueous displacement fluid comprises or consists of a, suitably inert, gas or a, suitably inert, liquid. More preferably the non-aqueous displacement fluid is a gas comprising or consisting of nitrogen, oxygen, carbon dioxide, air or a mixture thereof; or a liquid comprising or consisting of one or more alkanes.

Most preferably the non-aqueous displacement fluid is a non-aqueous, suitably inert, liquid.

The non-aqueous displacement fluid is a non-aqueous, preferably hydrophobic, liquid having a density equal to or less than 1000 kilograms per cubic meter ($kg/m^3$), more preferably having a density of less than 950 kilograms per cubic meter ($kg/m^3$), even more preferably having a density of less than 900 kilograms per cubic meter ($kg/m^3$), and most preferable a liquid having a density equal to or less than 800 $kg/m^3$. Such density may for example be determined by ASTM method no. ASTM D1217-15.

Preferably the non-aqueous displacement fluid is non-aqueous liquid that is essentially a liquid at the temperatures as applied in the process according to the invention. Preferably the non-aqueous displacement fluid has a boiling temperature at ambient pressure (i.e. at 1 bar corresponding to 0.1 MegaPascal) of equal to or more than 30° C., more preferably equal to or more than 50° C., even more preferably equal to or more than 80° C. and still more preferably equal to or more than 100° C.

Preferably the non-aqueous displacement fluid has a melting temperature at ambient pressure (i.e. at 1 bar corresponding to 0.1 MegaPascal) of equal to or less than 0° C., more preferably equal to or less than minus 5 degrees Celsius (−5° C.), even more preferably equal to or less than minus 10 degrees Celsius (−10° C.) and still more preferably equal to or less than minus 20 degrees Celsius (−20° C.).

Preferably the non-aqueous displacement fluid has no flash point or a flash point equal to or more than 60° C., even more preferably equal to or more than 80° C. and still more preferably equal to or more than 100° C. Such a flashpoint may for example be determined by ASTM method no. ASTM D93.

Preferably the non-aqueous displacement fluid has a viscosity at 20° C. of equal to or less than 5.0 centipoise (cP), more preferably equal to or less than 4.0 cP and most preferably equal to or less than 2 cP. Such viscosity may for example be determined by ASTM method no. ASTM D445-17a.

Preferably the non-aqueous displacement fluid comprises or consists of one or more alkanes, more preferably one or more alkanes having in the range from equal to or more than 5 to equal to or less than 20 carbon atoms, even more preferably an alkane having in the range from equal to or more than 6 to equal to or less than 16 carbon atoms. The alkanes may be cyclic or non-cyclic. Most preferably the non-aqueous displacement fluid comprises or consists of one or more alkanes chosen from the group consisting of cyclic hexane, normal hexane, iso-hexane and other hexanes, normal heptane, iso-heptane and other heptanes, normal octane, iso-octane and other octanes, normal nonane, iso-nonane and other nonanes, normal decane, iso-decane and other decanes, normal undecane, iso-undecane and other undecanes, normal dodecane, iso-dodecane and other dodecanes, normal tridecane, iso-tridecane and other tridecanes, normal tetradecane, iso-tetradecane and other tetradecanes, normal pentadecane, iso-pentadecane and other pentadecanes, normal hexadecane, iso-hexadecane and other hexadecanes.

More preferably the non-aqueous displacement fluid comprises or consists of one or more alkanes having in the range from equal to or more than 10 to equal to or less than 20 carbon atoms, even more preferably an alkane having in the range from equal to or more than 10 to equal to or less than 16 carbon atoms. Heavier alkanes having a lower flame point, such as the decanes, undecanes, dodecanes, tridecanes, tetradecanes, pentadecanes, hexadecanes and/or mixtures thereof, are preferred over the lighter alkenes having a higher flame point, such as the hexanes, heptanes, octanes, nonanes and mixtures thereof.

It is possible to use a non-halogenated alkane or a halogenated alkane. Preferably a non-halogenated alkane is used, but good results can also be achieved with for example perfluorohexane (i.e. 1,1,1,2,2,3,3,4,4,5,5,6,6,6-tetradecafluorohexane).

In an alternative embodiment according to the invention, the non-aqueous displacement fluid comprises or consists of an inert gas. For example, the non-aqueous displacement fluid can comprise or consist of nitrogen, oxygen, carbon dioxide or air.

The non-aqueous displacement fluid may suitably be displaced again from the remaining solid material in step (iii). It can be convenient to re-use the non-aqueous displacement fluid. In such a case, non-aqueous displacement fluid can be retrieved from step (iii) and recycled to step (ii). In such as case, the non-aqueous displacement fluid in step (ii) is a non-aqueous displacement fluid recycled from step (iii). The non-aqueous displacement fluid retrieved from step (iii) can optionally be purified and/or can optionally be stored in a displacement fluid storage vessel before being recycled to step (ii).

The non-aqueous displacement fluid can be supplied to any reactor which comprises a cylindrical vessel with its axis arranged in an essentially vertical manner. The non-aqueous displacement fluid is a non-aqueous, preferably hydrophobic, liquid having a density equal to or less than 1000 kilograms per cubic meter ($kg/m^3$), more preferably having a density of less than 950 kilograms per cubic meter ($kg/m^3$), even more preferably having a density of less than 900 kilograms per cubic meter ($kg/m^3$), Following the differences in density between the non-aqueous displacement fluid and the aqueous solution containing hydrochloric acid and dissolved saccharides (the first lighter than the second) it helps in maintaining a plug of liquid during the operation to supply the non-aqueous displacement fluid in a downward fashion (i.e. at the top of said reactor). Hence, now a vertical or essentially vertically directed reactor is used, the non-aqueous displacement fluid may for example be supplied to such reactor in a downward fashion.

The displacement can already be effected by the mere contacting of the non-aqueous displacement fluid with the pre-hydrolyzed solid material. To obtain the best results, the pre-hydrolyzed solid material is preferably soaked in non-aqueous displacement fluid. Following the same difference in density between non-aqueous displacement fluid and aqueous solution comprising hydrochloric acid solution (which also applies to the second aqueous hydrochloric acid solution, which will have a higher density than the non-aqueous displacement fluid) the second aqueous solution comprising hydrochloric acid is preferably pumped into the reactor from the bottom. Hence, in the present process it is preferred that the displacement fluid after step (ii) is removed from the top of the reactor by pumping the second aqueous hydrochloric acid solution into the reactor from the bottom. In such process step, it is preferred that the second aqueous hydrochloric acid solution is pumped into the reactor only after the displacement fluid in step (ii) has reached the bottom of the reactor, as then it is ensured that as much as possible of the first aqueous hydrochloric acid containing solution has been displaced from the reactor by the non-aqueous displacement fluid. Thus, in the process according to the present invention it is preferred that after the displacement fluid supplied from the top of the reactor in step (ii) has reached the bottom of the reactor, supplying displacement fluid in step (ii) is stopped and the pumping in of the second aqueous hydrochloric acid solution is started. Consequently, it is preferred that in such process as set out in the previous sentence, the second aqueous hydrochloric acid solution is preferably pumped into the reactor from the bottom.

Step (ii) can conveniently be carried out at about ambient temperature (20° C.). For practical purposes step (ii) is preferably carried out at a temperature equal to or less than 40° C., preferably equal to or less than 30° C. Most preferably step (ii) is carried out at a temperature in the range from equal to or more than 0° C. to equal to or less than 30° C.

Step (iii) suitably comprises hydrolyzing, at a temperature equal to or less than 40° C., preferably equal to or less than 30° C., at least part of the cellulose of the remaining solid material by replacing the non-aqueous displacement fluid with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution. Step (iii) suitably yields an aqueous second hydrolysate product solution and a residue.

As explained above, the hydrolysis of cellulose is also known as "main hydrolysis" and the products of the hydrolysis of cellulose are also known as "main hydrolysate". Step (iii) is therefore herein also referred to as "main hydrolysis". The second hydrolysate product solution obtained by hydrolysis of the cellulose in step (iii) is the second hydrolysate product solution obtained in the process. It can herein also be referred to as "main hydrolysate", "main hydrolysate solution" or "main hydrolysate product solution. As explained above, such main hydrolysis yields predominantly glucose and its oligomers as saccharides in the main hydrolysate.

During such main hydrolysis, a substantial part of the remaining bonds between the saccharide units in the remaining polysaccharides, are hydrolyzed. Although most preferably essentially all remaining bonds between the saccharide units in the remaining polysaccharides are broken, the advantages of the invention can also be obtained when a part of the bonds between such saccharide units remains intact.

The further hydrolyzing, respectively main hydrolysis, of the cellulose in the remaining solid material in step (iii) can already be effected by the mere contacting of the remaining solid material with the second aqueous hydrochloric acid solution.

Step (iii) can therefore conveniently be carried out at about ambient temperature (20° C.). For practical purposes step (iii) is preferably carried out at a temperature in the range from equal to or more than 0° C. to equal to or less than 30° C.

Step (iii) can be carried out over a wide range of pressures. Conveniently a pressure of about 0.1 MegaPascal (corresponding to about 1 bar) can be applied.

The hydrochloric acid concentration for the second aqueous hydrochloric acid solution as indicated above is based on the weight amount of water and hydrochloric acid contained in the second aqueous hydrochloric acid solution.

Preferably the second aqueous hydrochloric acid solution has a hydrochloric acid concentration in the range from equal to or more than 41.0 wt. % to equal to or less than 45.0 wt. %, based on the combined weight amount of water and hydrochloric acid in the second aqueous hydrochloric acid solution.

During step (iii) cellulose is being hydrolyzed and the resulting saccharides become dissolved in the second aqueous hydrochloric acid solution. Therefore, in addition to the water and the hydrochloric acid, the second aqueous hydrochloric acid solution may or may not contain other compounds such as for example dissolved saccharides.

When freshly added to the process, the second aqueous hydrochloric acid solution (also referred to as fresh second aqueous hydrochloric acid solution) preferably comprises only minor amounts or even essentially no dissolved saccharides.

After absorbing saccharides, the second aqueous hydrochloric acid solution is no longer fresh. Such a second aqueous hydrochloric acid solution that further contains dissolved saccharides is herein also referred to as "intermediate hydrolysate solution" or "intermediate main hydrolysate solution". The intermediate hydrolysate solution can suitably contain saccharides (such as a mixture of $C_6$-saccharides) dissolved in an aqueous hydrochloric acid solution. Such intermediate hydrolysate solution may therefore also be referred to as an, hydrochloric acid-containing, aqueous intermediate hydrolysate solution. The intermediate hydrolysate solution may suitably still be used for contacting further, optionally partly hydrolyzed, solid material to suitably absorb further saccharides therefrom.

To obtain the best results, the remaining solid material is preferably soaked in second aqueous hydrochloric acid solution. Such second aqueous hydrochloric acid solution may or may not contain saccharides.

Step (iii) suitably yields an aqueous second hydrolysate product solution and a residue. The second hydrolysate product solution is suitably an aqueous solution. As explained, one skilled in the art will understand that such solution suitably contains the products of the hydrolysis of the cellulose.

The residue may suitably comprise predominantly lignin. Preferably the residue contains mere minor amounts or essentially no hemicellulose and mere minor amounts or essentially no cellulose. Preferably, the cellulose content of the remaining solid material (which was used at the start of step (iii) has been reduced by at least at least 85 wt. %, more preferably at least 95 wt. %, and preferably essentially 100 wt. %. That is, preferably at least 85 wt. %, more preferably at least 95 wt. %, and most preferably essentially 100 wt. % of the cellulose in the remaining solid material is hydrolyzed in step (iii). The residue may thus comprise equal to or less than 10 wt. %, more preferably equal to or less than 5 wt. %, most preferably equal to or less than 1 wt. % of the cellulose that was present in the pre-hydrolyzed solid material. Most preferably the residue comprises essentially no cellulose and essentially no hemicellulose. The residue may in addition comprise hydrochloric acid.

The second hydrolysate product solution may suitably comprise or consist of an aqueous solution containing hydrochloric acid and predominantly glucose saccharides.

Preferably the second hydrolysate product solution contains a total amount of saccharides (including mono-, di- and/or oligosaccharides) of equal to or more than 2 wt. % saccharides, more preferably of equal to or more than 5 wt. % saccharides, still more preferably of equal to or more than 10 wt. % saccharides, and most preferably of equal to or more than 20 wt. % saccharides, based on the total weight of the second hydrolysate solution. The upper limit for the saccharide content in the second hydrolysate product solution is formed by the solubility of the saccharides in the solution. For glucose, a solubility at 25° C. of 909 grams glucose per kilogram water has been reported. For practical purposes the second hydrolysate product solution may suitably contain a total amount of saccharides (including mono-, di- and/or oligosaccharides) of equal to or less than 45 wt. %, more preferably of equal to or less than 40 wt. % saccharides, based on the total weight of the second hydrolysate solution.

The second hydrolysate product solution may include for example glucose monosaccharides, glucose disaccharides, and glucose oligosaccharides. Suitably the second hydrolysate product solution can comprise one or more compounds selected from the group consisting of glucose and cellobiose.

The second hydrolysate product solution may comprise some, but preferably comprises little or no pentoses (C5-saccharides). Preferably, the second hydrolysate product solution contains a total amount of C5-saccharides, that is equal to or less than 20.0 wt. %, more preferably equal to or less than 10.0 wt. %, still more preferably equal to or less than 5.0 wt. %, even more preferably equal to or less than 1.0 wt. % and most preferably equal to or less than 0.1 wt. %, based on the total weight of saccharides in the second hydrolysate solution.

In addition to the saccharides, the second hydrolysate product solution will suitably contain hydrochloric acid. Preferably the second hydrolysate product solution will have a hydrochloric acid concentration in the range from equal to or more than 20.0 wt. %, more suitably equal to or more than 30.0 wt. % to equal to or less than 50.0 wt. %, more suitably equal to or less than 45.0 wt. %, more preferably in the range from equal to or more than 38.0 wt. % to equal to or less than 43.0 wt. %, based on the weight of the combination of hydrochloric acid and water.

Optionally, the process according to the invention may further comprise an additional step (iv) comprising displacing aqueous solution(s) from the residue with additional non-aqueous displacement fluid. Such additional non-aqueous displacement fluid can be the same or different from the non-aqueous displacement fluid used in step (ii). Preferences for this additional non-aqueous displacement fluid in an optional step (iv) are as described above for the non-aqueous displacement fluid used in step (ii). Also temperature, pressure and other preferences for such an optional step (iv) are the same as described above for step (ii). If a step (iv) is included, the non-aqueous displacement fluid may after completion of such step (iv) be drained or otherwise removed from the residue again.

The process can further comprise an additional step wherein the residue is unloaded from the reactor involved. The residue may subsequently be washed and/or incinerated. As described above, the residue may suitably comprise predominantly lignin.

It is further believed that this lignin composition may be novel and inventive in itself. Suitably the invention therefore further provides a lignin composition, obtainable by a process as described herein. Suitably such a lignin composition can advantageously have a reduced sugar content and/or a reduced hydrochloric acid content, when compared to a lignin composition that has not been treated with a displacement fluid.

Suitable processes for obtaining a saccharide product from the pre-hydrolysate solution (i.e. the first hydrolysate product solution) and/or the main hydrolysate solution (i.e. the second hydrolysate solution) are described in for example WO2017/082723 and WO2016/099272. Preferably the pre-hydrolysate solution and/or the main hydrolysate solution is suitably first admixed with a carrier liquid, in which the saccharides are insoluble and that has a boiling point higher than that of water to obtain an aqueous admixture. Subsequently such aqueous admixture can be subjected to an evaporation step, to yield a vapor fraction comprising water and hydrochloric acid and a residue fraction comprising solid saccharides and the carrier liquid. The vapor fraction may advantageously be condensed, reconcentrated and recycled to the process to be used as a first or second hydrochloric acid solution. The residue fraction comprising solid saccharides and the carrier liquid can conveniently be recovered and passed to a separation vessel. Such a separation vessel can for example be a settling vessel or any other separator that is suitable to separate the saccharides from the carrier liquid. From the separation vessel a saccharide product can be obtained. In addition a stream of crude carrier liquid can be obtained that can be cleaned and recycled. Thus, preferably the process according to invention comprises one or more further steps wherein:

the first hydrolysate product solution and/or the second hydrolysate product solution is/are admixed with a carrier liquid, in which saccharides are insoluble and that has a boiling point higher than that of water to obtain an aqueous admixture;

the aqueous admixture is subjected to an evaporation step, to yield a vapor fraction comprising water and hydrochloric acid and a residue fraction comprising solid saccharides and the carrier liquid; and the residue fraction comprising solid saccharides and the carrier liquid is passed to a separation vessel to obtain a saccharides product.

It is believed that this saccharides product may be novel and inventive in itself. Suitably the invention therefore further provides a saccharide composition, obtainable by a process as described herein.

As explained above, the process according to the invention can be carried out in one or more reactors.

Preferably the solid material remains stationary within such one or more reactors, whilst being contacted with one or more moving portions of the first aqueous hydrochloric acid solution; and/or one or more moving portions of the non-aqueous displacement fluid; and/or one or more moving portions of the second aqueous hydrochloric acid solution.

More preferably the solid material is residing in a stationary phase within a reactor and is contacted with a mobile phase that moves through such reactor, which mobile phase includes:

a zone comprising one or more portions of first aqueous hydrochloric acid solution; preferably followed by a zone comprising one or more portions of a liquid non-aqueous displacement fluid; preferably followed by a zone comprising one or more portions of second aqueous hydrochloric acid solution.

By followed is herein understood that the subsequent zone is contacted with the solid material at a point in time later than the point in time where the solid material was contacted with the preceding zone.

More preferably the solid material is residing in a stationary phase within a reactor and
is contacted with a mobile phase that moves through such reactor, which mobile phase includes:
a) a zone comprising one or more portions of an intermediate pre-hydrolysate solution; preferably followed by
b) a zone comprising one or more portions of, preferably fresh, first aqueous hydrochloric acid solution; preferably followed by
c) a zone comprising one or more portions of a liquid non-aqueous displacement fluid; preferably followed by
d) a zone comprising one or more portions of an intermediate hydrolysate solution; preferably followed by
e) a zone comprising one or more portions of, preferably fresh, second aqueous hydrochloric acid solution; optionally followed by
f) an optional zone comprising one or more further portions of additional liquid non-aqueous displacement fluid.

Without wishing to be bound by any kind of theory it is believed that the use of such a mobile phase conveniently allows each subsequent zone to displace the preceding zone from the solid material.

Conveniently the solid material containing hemicellulose, cellulose and lignin can be residing in a stationary phase within vertical a reactor, and can be contacted in step (i) with one or more zones of a mobile phase that moves through such reactor, including a zone comprising one or more portions of an intermediate pre-hydrolysate solution and/or a zone comprising one or more portions of, preferably fresh, first aqueous hydrochloric acid solution, to yield an aqueous first hydrolysate product solution and pre-hydrolyzed solid material. The zones of the mobile phase can suitably be the zones a) and b) as described above.

Subsequently, any aqueous solution(s) can be displaced from the remaining solid material with a non-aqueous displacement fluid, by contacting such remaining solid material in step (ii) with a subsequent zone of the mobile phase that moves in a downward fashion through such reactor, which subsequent zone comprises one or more portions of a liquid non-aqueous displacement fluid by contacting such remaining solid material in step (ii) with a subsequent zone of the mobile phase that moves through such reactor, which subsequent zone comprises one or more portions of a liquid non-aqueous displacement fluid. It is to be noted that in this case the remaining solid material may suitably still be residing in a stationary phase in the reactor. This zone of the mobile phase can suitably be the zone c) as described above.

Subsequently the non-aqueous displacement fluid can be displaced from the remaining solid material with a second aqueous hydrochloric acid solution, by contacting the remaining solid material in step (iii) with one or more subsequent zones of the mobile phase that moves through such reactor, including a zone comprising one or more portions of an intermediate hydrolysate solution and/or a zone comprising one or more portions of, preferably fresh, second aqueous hydrochloric acid solution, to yield an aqueous second hydrolysate product solution and a residue. It is to be noted that such remaining solid material may suitably still be residing in a stationary phase in the reactor. The zones of the mobile phase can suitably be the zones d) and e) as described above.

Subsequently, optionally, the second hydrolysate solution can be displaced from the residue, by contacting such residue in an optional step (iv) with a subsequent zone of the mobile phase that moves through such reactor in a downward fashion, which subsequent zone comprises one or more further portions of additional liquid non-aqueous displacement fluid. This zone of the mobile phase can suitably be the zone f) as described above.

In the above processes, the mobile phase can suitably be an intermittent, semi-continuous or continuous mobile phase. Preferably the mobile phase is a semi-continuously or continuously moving mobile phase.

More preferably the process is carried out in a plurality of reactors. More preferably the process is carried out in a plurality of reactors connected in series, herein also referred to as a battery or series of reactors or as a reactor sequence.

Preferably, the process is carried out in a plurality of reactors (also referred to as columns) connected in series as described for a Bergius Rheinau process. Examples of the Bergius Rheinau process include the Bergius Rheinau process, preferably as amended by Riehm, as described in for example U.S. Pat. No. 2,778,751. It is also possible for the process to be carried out in a plurality of reactors as described in WO2012/061085.

Preferably the process is carried out in a plurality of reactors connected in series.

More preferably the process is carried out in a reactor sequence of two or more reactors, wherein during steps (i), (ii), (iii) solid material is residing stationary within each reactor, whilst the first aqueous hydrochloric acid solution and/or the non-aqueous displacement fluid and/or the second aqueous hydrochloric acid solution is/are passed, preferably in a continuous or semi-continuous fashion, from one reactor into another reactor.

In a preferred embodiment, following the differences in density between the non-aqueous displacement fluid and the (first and second) aqueous hydrochloric acid solutions, the presently claimed invention relates to a process for the conversion of a solid material containing hemicellulose, cellulose and lignin, which process comprises the following steps:

(i) hydrolyzing, at a temperature equal to or less than 40° C. at least part of the hemicellulose of the solid material by contacting the solid material with a first aqueous hydrochloric acid solution, which first aqueous hydrochloric acid solution has a hydrochloric acid concentration in the range from equal to or more than 15.0 wt. % to less than 40.0 wt. %, based on the weight amount of water and hydrochloric acid in such first aqueous hydrochloric acid solution, yielding a remaining solid material and an aqueous first hydrolysate product solution;

(ii) displacing the aqueous solution from the remaining solid material with a non-aqueous displacement fluid;

(iii) hydrolyzing, at a temperature equal to or less than 40° C. at least part of the cellulose of the remaining solid material by replacing the non-aqueous displacement fluid with a second aqueous hydrochloric acid solution, which second aqueous hydrochloric acid solution has a hydrochloric acid concentration in the range from equal to or more than 40.0 wt. % to equal to or less than 51.0 wt. %, based on the weight amount of water and hydrochloric acid in such second aqueous hydrochloric acid solution, yielding a residue and an aqueous second hydrolysate product solution, wherein process step (i) is carried out in at least one reactor of cylindrical shape with its axis arranged in an essentially vertical manner, and wherein said non-aqueous displacement fluid is a non-aqueous, preferably hydrophobic, liquid having a density equal to or less than 1000 kilograms per cubic meter ($kg/m^3$), preferably having a density of less than 950 kilograms per cubic meter ($kg/m^3$), more preferably having a density of less than 900 kilograms per cubic meter ($kg/m^3$), and wherein the non-aqueous displacement fluid is supplied to such reactor at the top of said reactor, pushing out said aqueous first hydrolysate product solution at the bottom from said reactor.

It is even more preferred in the above process that said non-aqueous displacement fluid is supplied at the top of said reactor until said non-aqueous displacement fluid exits the bottom of the reactor, at or after which moment the supply of non-aqueous displacement fluid at the top of said reactor is stopped and subsequently or simultaneously the second aqueous hydrochloric acid solution is supplied at the bottom of said reactor thereby reversing the flow of non-aqueous displacement fluid in an upward fashion and pushing out the non-aqueous displacement fluid at the top of the reactor.

Preferably the process is carried out in a plurality of reactors connected in series:
  wherein one or more portions of first aqueous hydrochloric acid solution are moving from one reactor to another and are contacted with, optionally partly pre-hydrolyzed, stationary solid lignocellulosic material, fixed in the reactors; and/or
  wherein one or more portions of second aqueous hydrochloric acid solution are moving from one reactor to another and are contacted with, optionally partly hydrolyzed, stationary pre-hydrolyzed solid material, fixed in the reactors. Preferably the one or more portions of first aqueous hydrochloric acid solution and/or the one or more portions of second aqueous hydrochloric acid solution are moving in a continuous or semi-continuous fashion.

More preferably, the first aqueous hydrochloric acid solution is contacted counter-currently with the, optionally partly pre-hydrolyzed, solid lignocellulosic material; and/or, the second aqueous hydrochloric acid solution is contacted counter-currently with the, optionally partly hydrolyzed, pre-hydrolyzed solid material.

The portions of first and/or second aqueous hydrochloric acid solution are preferably followed by one or more portions of a non-aqueous displacement fluid.

Hence, in step (i) one or more portions of first aqueous hydrochloric acid solution can conveniently form a plug or liquid column, optionally in combination with a non-aqueous displacement fluid, which plug or liquid column is travelling continuously or semi-continuously through a plurality of reactors, each reactor containing an amount of, optionally already partly pre-hydrolyzed, stationary solid lignocellulosic material (i.e. solid material containing cellulose, hemicellulose and lignin). When step (i) is carried out counter-currently, one or more portions of fresh first aqueous hydrochloric acid solution may conveniently be supplied to a reactor holding solid lignocellulosic material, where the hemicellulose in such solid lignocellulosic material has already been partly pre-hydrolyzed to the highest degree. Saccharides can be absorbed from such, already partly pre-hydrolyzed lignocellulosic material and the one or more portions of first aqueous hydrochloric acid solution (suitably now containing some saccharides) may subsequently move from the outlet of such reactor to the inlet of a preceding reactor, which preceding reactor holds lignocellulosic material which has undergone less pre-hydrolysis.

Whilst moving, preferably counter-currently, from each one reactor to another reactor the above first aqueous hydrochloric acid solution may suitably absorb more and more saccharides. Thus, the saccharide concentration of the first aqueous hydrochloric acid solution may suitably gradually increase until a hydrochloric acid-containing, aqueous first hydrolysate product solution is produced.

When carried out counter-currently, step (i) is preferably carried out in a plurality of "x" reactors $FR_1$ to $FR_x$, connected in series, wherein fresh lignocellulosic material can be introduced and/or residing in reactor $FR_1$ and each subsequent reactor $FR_2$ to $FR_x$ can contain partly pre-hydrolyzed lignocellulosic material, where the degree of pre-hydrolysis of the lignocellulosic material may increase in the direction of reactor $FR_2$ to $FR_x$; and wherein one or more portions of fresh first aqueous hydrochloric acid solution can be introduced in the last reactor $FR_x$ and can move counter-currently from reactor $FR_x$ to reactor $FR_1$. Suitably such portions of first aqueous hydrochloric acid solution can gradually absorb saccharides from the, optionally already partly pre-hydrolyzed lignocellulosic material, to thereby produce a hydrochloric acid-containing, aqueous pre-hydrolysate solution that can be withdrawn from reactor $FR_1$. Such hydrochloric acid-containing, aqueous pre-hydrolysate solution will advantageously be more rich in saccharides than if step (i) would have been carried out in a single reactor. In reactor $FR_x$ a prehydrolyzed solid material can be obtained, that can suitably be discarded from the reactor $FR_x$.

Similarly, in step (iii) one or more portions of second aqueous hydrochloric acid solution can conveniently form a plug or liquid column, optionally in combination with a non-aqueous displacement fluid, which plug or liquid column is travelling continuously or semi-continuously through a plurality of stationary reactors, each reactor containing an amount of, optionally already partly hydrolyzed, stationary remaining solid material (i.e. remaining solid material containing cellulose and lignin).

When step (iii) is carried out counter-currently, the one or more portions of fresh second aqueous hydrochloric acid solution may conveniently be supplied to a reactor holding remaining solid material which has already been partly hydrolyzed to the highest degree. Saccharides can be absorbed from such, already partly hydrolyzed, remaining solid material and the one or more portions of second aqueous hydrochloric acid solution (suitably now containing some saccharides) may subsequently move from the outlet of such reactor to the inlet of a preceding reactor, which preceding reactor holds remaining solid material which has undergone less hydrolysis.

Whilst moving, preferably counter-currently, from one reactor to another reactor the second aqueous hydrochloric acid solution may suitably absorb more and more saccharides. Thus, the saccharide concentration of the second aqueous hydrochloric acid solution may suitably gradually increase until a hydrochloric acid-containing, aqueous second hydrolysate product solution is produced.

When carried out counter-currently, step (iii) is preferably carried out in a plurality of "y" reactors $SR_1$ to $SR_y$, connected in series, wherein fresh remaining solid material is residing or is introduced in reactor $SR_1$ and each subsequent reactor $SR_2$ to $SR_y$ contains partly hydrolyzed, pre-hydrolyzed solid material, where the degree of hydrolysis of the remaining solid material increases in the direction of $SR_2$ to $SR_y$; and wherein one or more portions of fresh second aqueous hydrochloric acid solution are introduced in the last reactor $SR_y$ and move counter-currently from reactor $SR_y$ to reactor $SR_1$, and wherein such portions of second aqueous hydrochloric acid solution gradually absorb saccharides from the, optionally already partly hydrolyzed, pre-hydrolyzed solid material, to thereby produce a hydrochloric acid-containing, aqueous hydrolysate solution, that can be withdrawn from reactor $SR_1$. Such hydrochloric acid-containing, aqueous hydrolysate solution will be advantageously more rich in saccharides, than if step (iii) would have been carried out in a single reactor. In reactor $SR_y$ a hydrolyzed lignocellulosic material can be obtained, that can suitably be discarded from the reactor $SR_y$.

Preferably the process according to the invention is carried out in a plurality of reactors, connected in series, comprising 2 or more reactors, more preferably in the range from equal to or more than 2 to equal to or less than 16 reactors, still more preferably in the range from equal to or more than 4 to equal to or less than 8 reactors and most preferably in the range from equal to or more than 4 to equal to or less than 7 reactors.

It is possible for step (i) to be carried out in a first set of reactors connected in series and for step (iii) to be carried out in an, optionally separate, second set of reactors connected in series. Suitably each such a set of reactors comprises 2 or more reactors, preferably 2 to 10, more preferably 2 to 8 reactors and most preferably 2 to 4 reactors.

Preferably, however, step (i) and step (iii) are carried out within one combined set of reactors connected in series. Preferably such a combined set of reactors connected in series comprises 2 or more reactors, more preferably in the range from equal to or more than 2 to equal to or less than 16 reactors, still more preferably in the range from equal to or more than 4 to equal to or less than 8 reactors and most preferably in the range from equal to or more than 4 to equal to or less than 7 reactors.

When it is desirable for the process to be carried out in a continuous or semi-continuous manner in a plurality of reactors, it is important that one can adjust the flowrate such that the process in each reactor can be performed in an optimal manner. Without wishing to be bound by any kind of theory it is believed that as a consequence of the hydrolysis of the hemicellulose and the hydrolysis of the cellulose the volume of solid material in the reactors may shrink. To compensate it can be desirable to adjust the volume of non-aqueous displacement fluid being used.

The process according to the invention can advantageously be carried out in a continuous or semi-continuous manner. For example, the process can be carried out in a plurality of reactors in a sequence of cycles, wherein within each cycle:

at least part of the hemicellulose of a solid lignocellulosic material (that is, a solid material containing hemicellulose, cellulose and lignin) is hydrolysed in a first reactor sequence of "x" reactors $FR_1$ to $FR_x$, wherein fresh solid lignocellulosic material is introduced in reactor $FR_1$ and each subsequent reactor $FR_2$ to $FR_x$ contains, partly pre-hydrolyzed, solid material; and wherein one or more portions of, preferably fresh, first aqueous hydrochloric acid solution are introduced in the last reactor $FR_x$ pushing forward a first liquid column, such first liquid column containing previous portions of first aqueous hydrochloric acid solution, in a counter-current direction from reactor $FR_x$ to reactor $FR_1$; yielding a prehydrolyzed solid material residing in reactor $FR_x$ and a hydrochloric acid-containing, aqueous first hydrolysate product solution residing in reactor $FR_1$, whereafter the hydrochloric acid-containing, aqueous first hydrolysate product solution is recovered from reactor $FR_1$ and any aqueous solutions are displaced from the prehydrolyzed solid material with a, suitably first, non-aqueous displacement fluid in reactor $FR_x$;

at least part of the cellulose of a prehydrolyzed solid material is hydrolysed in a second reactor sequence of "y" reactors $SR_1$ to $SR_y$, wherein fresh prehydrolyzed solid material is residing in reactor $SR_1$ and each subsequent reactor $SR_2$ to $SR_y$ contains, partly hydrolysed, prehydrolyzed solid material; and wherein one or more portions of, preferably fresh, second aqueous hydrochloric acid solution are introduced in the last reactor $SR_y$ pushing forward a second liquid column, such second liquid column containing previous portions of second aqueous hydrochloric acid solution, in a counter-current direction from reactor $SR_y$ to reactor $SR_1$; yielding a residue residing in reactor $SR_y$ and a hydrochloric acid-containing, aqueous second hydrolysate product solution residing in reactor $SR_1$; whereafter the hydrochloric acid-containing, aqueous second hydrolysate product solution is recovered from reactor $SR_1$; and optionally any aqueous solutions(s) are displaced from the residue with a, suitably second, non-aqueous displacement fluid in reactor $SR_y$ and thereafter unloaded from reactor $SR_y$;

whereafter
respective reactors $FR_1$ to $FR_{x-1}$ shift into the position of respective reactors $FR_2$ to $FR_x$,
respective reactor $FR_x$ shifts into the position of respective reactor $SR_1$,
respective reactors $SR_1$ to $SR_{y-1}$ shift into the position of respective reactors $SR_2$ to $SR_y$, and
respective reactor $SR_y$ shifts into the position of respective reactor $FR_1$.

By shifting of one reactor into the position of another reactor is herein preferably understood that the one reactor takes over the place, i.e. the function, of the other reactor in the mentioned first or second reactor sequence.

Each cycle is preferably performed within a time period referred to as the cycle period. The cycle period preferably lies in the range of equal to or more than 4 hours, more preferably equal to or more than 6 hours, to equal to or less than 24 hours, more preferably equal to or less than 12 hours. Most preferably the cycle period lies in the range from equal to or more than 7 hours to equal to or less than 9 hours. For example, the cycle period can be 8 hours.

The partly remaining solid material initially residing in reactors $FR_2$ to $FR_x$ can conveniently be obtained in one or more previous cycle periods.

Similarly, the partly hydrolyzed, remaining solid material initially residing in reactors $SR_2$ to $SR_y$ can be suitably obtained in one or more previous cycle periods.

Preferences for the reaction conditions, the lignocellulosic material, the first aqueous hydrochloric acid solution, the second aqueous hydrochloric acid solution, the first hydrolysate product solution, the second hydrolysate product solution, the remaining solid material and the non-aqueous displacement fluids, any mobile phases and any other aspects are all as described herein above.

During a cycle period, the rate at which the reactants are provided to the reactors can vary widely, especially as some reactants such as wood may be provided to the reactors at an intermittent basis. When averaged over a full cycle period, the average weight ratio of amount of first aqueous hydrochloric acid solution to amount of solid (lignocellulosic) material (on dry basis) preferably lies in the range from equal to or more than 0.5:1 (wt/wt) to equal to or less than 10:1(wt/wt), more preferably equal to or less than 7:1 (wt/wt) and most preferably equal to or less than 5:1(wt/wt). Similarly, when averaged over a full cycle period, the average weight ratio of amount of second aqueous hydrochloric acid solution to amount of solid (lignocellulosic) material (on dry basis) preferably lies in the range from equal to or more than 0.5:1 (wt/wt) to equal to or less than 10:1(wt/wt), more preferably equal to or less than 7:1(wt/wt) and most preferably equal to or less than 5:1(wt/wt).

When averaged over a full cycle period, the average weight ratio of amount of non-aqueous displacement fluid to amount of lignocellulosic material preferably lies in the range from equal to or more than 2:1 (wt/wt) to equal to or less than 4:1 (wt/wt).

EXAMPLE 1

Non-limiting FIGS. 1A, 1B, 1C, 2A and 2B illustrate an example of the process according to the invention.

The illustrated process is carried out in a reactor sequence of 6 hydrolysis reactors (R1 to R6). The hydrolysis reactors are operated at a temperature of 20° C. and a pressure of 0.1 MegaPascal. The process is operated in a sequence of cycles, each cycle being carried out within a 8 hour cycle period.

FIG. 1A illustrates the start of a new cycle. At the start of a new cycle, dried wood chips (101) have just been loaded into reactor (R1) via solid inlet line (102). Reactor (R2) contains an intermediate prehydrolysate solution and a solid material containing cellulose and lignin. The hemicellulose is already at least partly hydrolysed. Reactor (R3) contains a displacement fluid (such as for example iso-octane) and a solid material containing cellulose and lignin. Reactors (R4) and (R5) each contain an intermediate hydrolysate solution. The intermediate hydrolysate solution in reactor (R4) can contain a higher amount of saccharides than the intermediate hydrolysate solution in reactor (R5), as explained below. In addition reactors (R4) and (R5) contain a solid material containing lignin. The cellulose is already at least partly hydrolysed. Reactor (R6) contains a displacement fluid (such as for example iso-octane) and a residue. The residue is a solid material containing lignin.

Figure 1B:
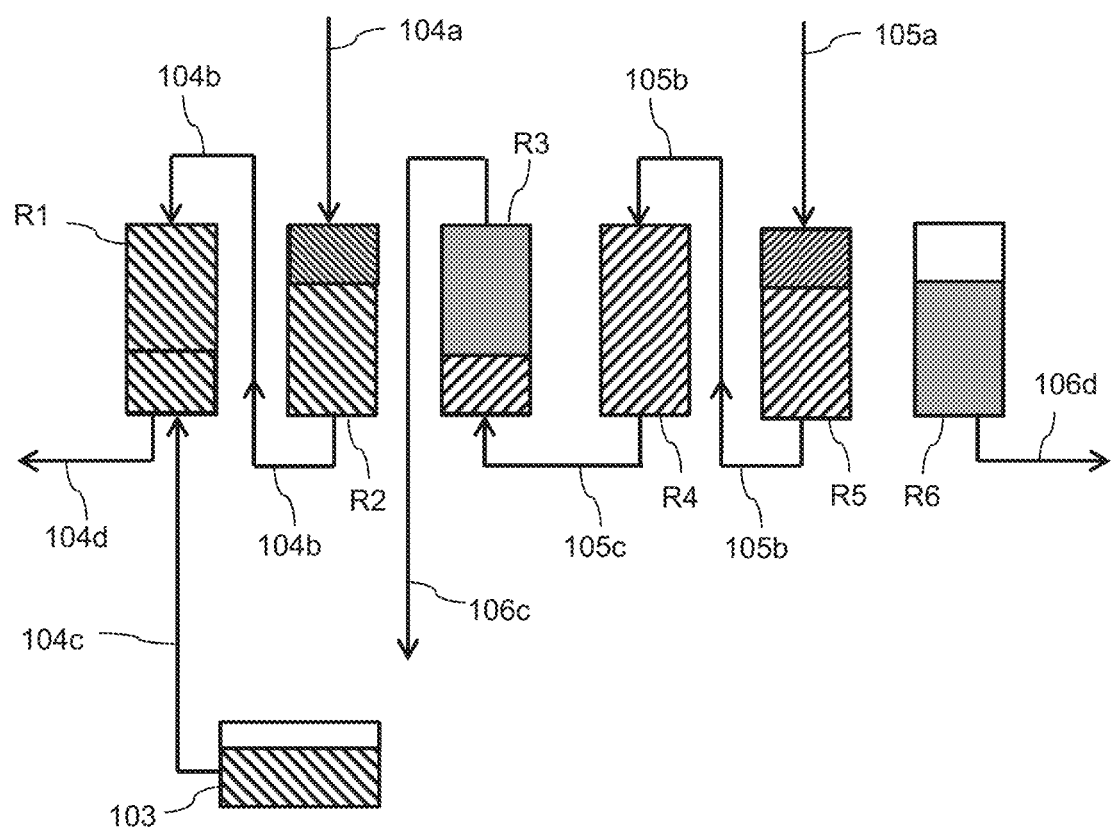

As illustrated in FIG. 1B, during a first part of the cycle, reactor (R1) is flooded with a plug (104c) of intermediate prehydrolysate solution coming from a storage vessel (103), a plug (104a) of fresh first aqueous hydrochloric acid solution is introduced to reactor (R2), a plug (105a) of fresh second aqueous hydrochloric acid solution is introduced to reactor (R5) and a plug (106d) of displacement fluid is drained from reactor (R6).

After reactor (R1) has been flooded with a plug (104c when going into R1, 104d when being pushed out of R1) of intermediate prehydrolysate solution coming from a storage vessel (103), a plug (104a) of fresh first aqueous hydrochloric acid solution, having a hydrochloric acid concentration of 37.0 wt. % and containing essentially no saccharides yet, is introduced into reactor (R2), thereby pushing forward a plug (104b) of intermediate pre-hydrolysate solution, containing hydrochloric acid in a concentration of about 37.0 wt. %, but also containing already some saccharides (i.e. saccharides derived from solid material that was residing in reactor (R2)), from reactor (R2) into reactor (R1). The plug (104b) of intermediate pre-hydrolysate solution, pushes the plug (104d) out from reactor (R1). Plug (104d) previously contained intermediate pre-hydrolysate solution, but has now taken up sufficient saccharides and has become a final first hydrolysate product solution. Such final first hydrolysate product solution can suitably be forwarded to one or more subsequent processes or devices, where optionally hydrochloric acid could be removed from the pre-hydrolysate solution and recycled.

During the same first part of the cycle, a plug (105a) of fresh second aqueous hydrochloric acid solution, having a hydrochloric acid concentration of 42.0 wt. % and containing essentially no saccharides yet, is introduced into reactor (R5), thereby pushing forward a plug (105b) of intermediate hydrolysate solution, containing hydrochloric acid in a concentration of about 42.0 wt. %, but also containing already some saccharides (i.e. derived from the solid material that was residing in reactor (R5)), from reactor (R5) into reactor (R4). This plug (105b) in its turn pushes forward a second plug (105c) of intermediate hydrolysate solution, containing hydrochloric acid in a concentration of about 42.0 wt. %, but also containing saccharides (i.e. derived from solid material that was residing in previous reactors), from reactor (R4) into reactor (R3). Whilst being pushed from reactor (R5) into reactor (R4) and further into reactor (R3), the intermediate hydrolysate solution absorbs more and more saccharides from the solid material remaining in such reactors from previous stages. The saccharide concentration of the intermediate hydrolysate solution advantageously increases, thus allowing a saccharide concentration to be obtained, that is higher than the saccharide concentration obtained in a batch-process.

The plug (105c) of intermediate hydrolysate solution being pushed from reactor (R4) into reactor (R3), pushes a plug (106c) of displacement fluid out of reactor (R3).

During this same first part of the cycle, further a plug (106d) of displacement fluid is drained from reactor (R6), leaving behind a residue containing lignin.

Figure 1C:
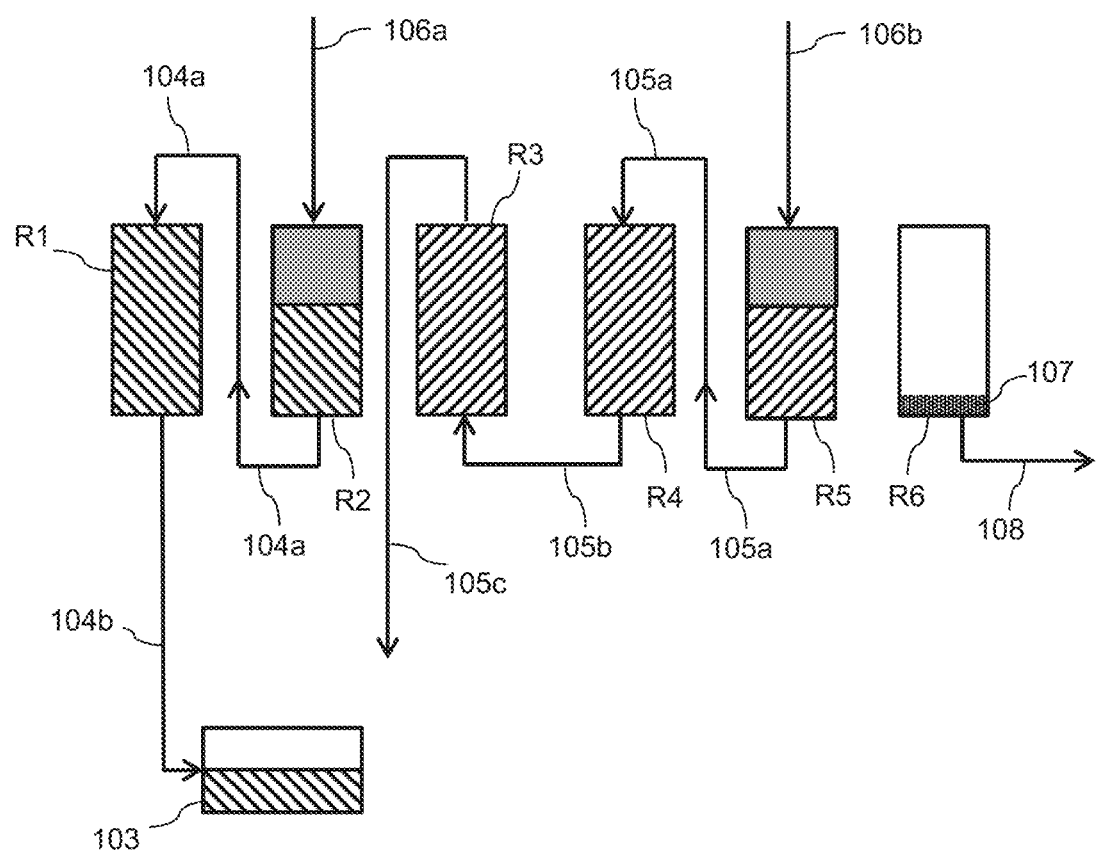

During a second part of the cycle, as illustrated by FIG. 1C, a plug (106a) of displacement fluid is introduced into reactor (R2). This plug (106a) may or may not contain parts of the plug (106c) of displacement fluid that was pushed out of reactor (R3). Advantageously, the volume of displacement fluid in plug (106a) can be adjusted, for example by adding more or less displacement fluid, to compensate for volume losses due to the reduction of solid material volume. This allows one to ensure that all reactors remain sufficiently filled with volume and it allows one to maintain a sufficient flowrate.

The plug (106a) of displacement fluid being introduced in reactor (R2), suitably pushes forward plug (104a) that was residing in reactor (R2). Plug (104a), previously contained merely fresh first aqueous hydrochloric acid solution, but has in the meantime taken up saccharides from the solid material in reactor (R2) and has become an intermediate pre-hydrolysate solution. Plug (104a) is pushed out of reactor (R2) into reactor (R1), thereby pushing forward plug (104b) of intermediate pre-hydrolysate solution out of reactor (R1) into storage vessel (103) as illustrated in FIG. 1C.

In addition, suitably, a plug of displacement fluid (106b) is introduced into reactor (R5). The plug (106b) of displacement fluid being introduced in reactor (R5), suitably pushes forward plug (105a) that was residing in reactor (R5). Plug (105a), previously contained merely fresh second aqueous hydrochloric acid solution, but has in the meantime taken up saccharides from the solid material in reactor (R5) and has become an intermediate hydrolysate solution. Plug (105a) is pushed out of reactor (R5) into reactor (R4), thereby pushing forward plug (105b) of intermediate pre-hydrolysate solution out of reactor (R4) into reactor (R3). The plug (105b) of intermediate pre-hydrolysate solution, pushes forward plug (105c) that was residing in reactor (R3). Plug (105c), previously contained intermediate hydrolysate solution, but has now taken up sufficient saccharides and has become an aqueous second hydrolysate product solution. Such second hydrolysate product solution can also be referred to as a hydrolysate product solution. Plug (105c) of second hydrolysate product solution is pushed out from reactor (R3). Such second hydrolysate product solution can suitably be forwarded to one or more subsequent processes or devices, where optionally hydrochloric acid could be removed from the hydrolysate solution and recycled.

Figure 2A:
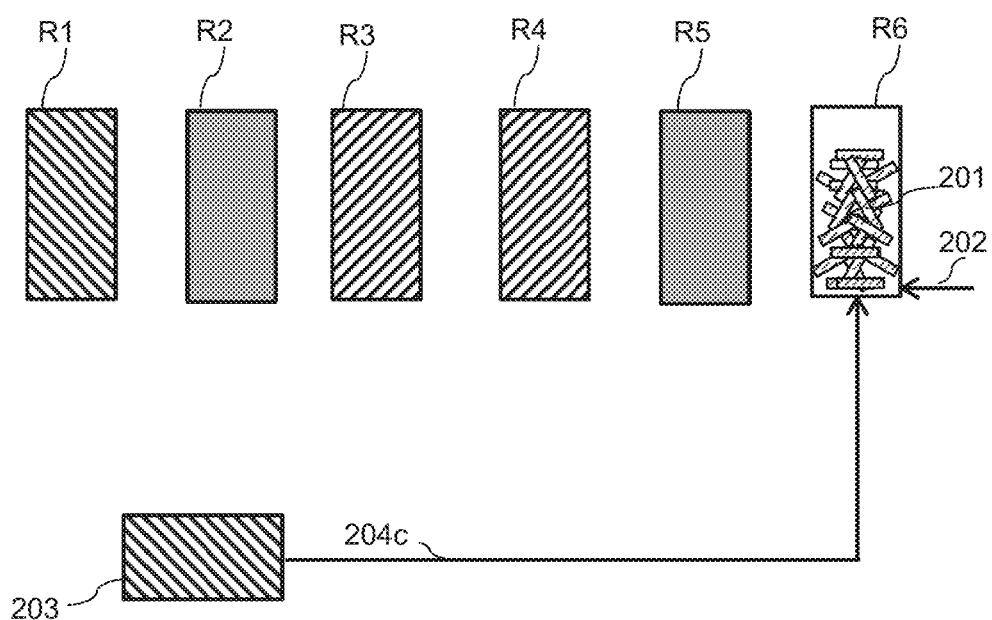
FIGS. 2A and 2B illustrate a second subsequent cycle, starting at a time "t+8 hours", of the same process as FIGS. 1A, 1B and 1C.

During this same second part of the cycle, residue (107) containing lignin can suitably be removed from reactor (R6) via solid outlet line (108) and reactor (R6) can be loaded with a new batch of dried wood chips (shown as (201) in FIG. 2A).

The cycle has now been completed and all reactors have shifted one position in the reactor sequence. That is:
reactor (R6) has now shifted into the position previously occupied by reactor (R1);
reactor (R1) has now shifted into the position previously occupied by reactor (R2);
reactor (R2) has now shifted into the position previously occupied by reactor (R3);
reactor (R3) has now shifted into the position previously occupied by reactor (R4);
reactor (R4) has now shifted into the position previously occupied by reactor (R5); and
reactor (R5) has now shifted into the position previously occupied by reactor (R6).

As indicated, the above cycle takes about 8 hours. A subsequent cycle can now be started.

Figure 2B:
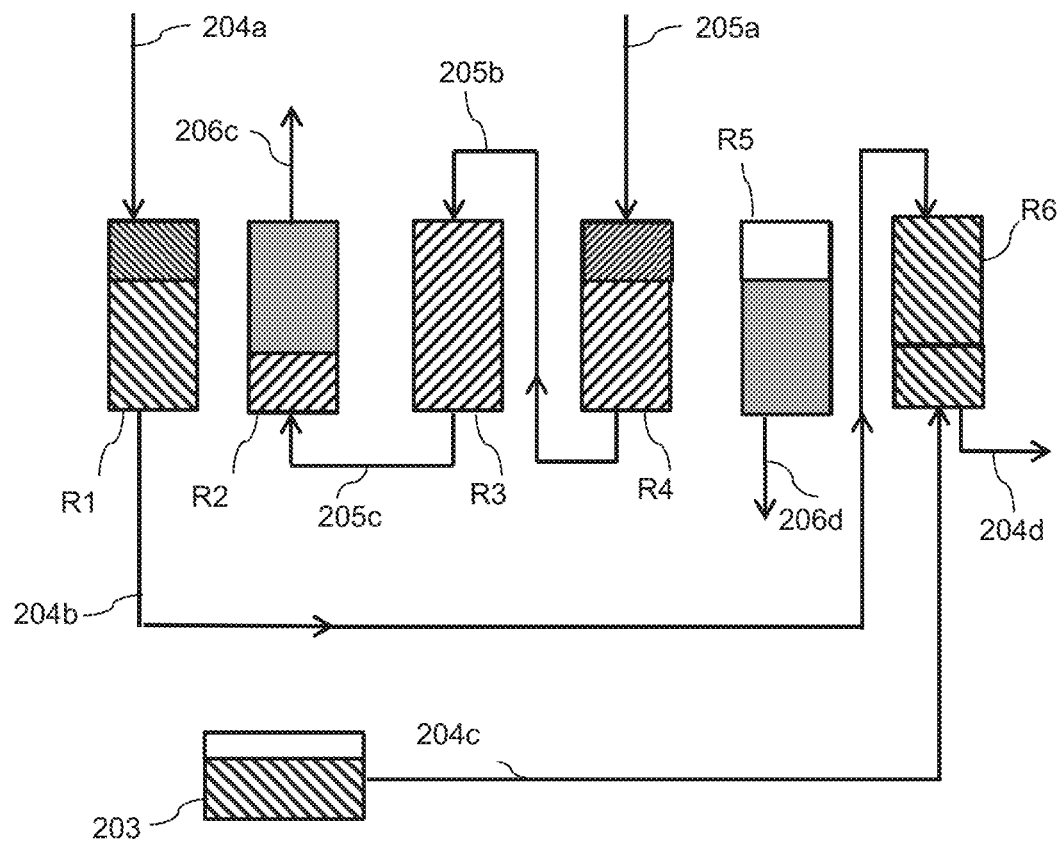

The situation wherein all reactors have shifted one position has been illustrated in FIG. 2A. FIG. 2A illustrates the start of a subsequent cycle, at a time "t+8 hours". The dried wood chips in what was previously reactor (R6) and is now reactor (R1) can be flooded with a plug (204c) of intermediate pre-hydrolysate solution withdrawn from the storage vessel (203). This is the same intermediate pre-hydrolysate solution that was stored in such storage vessel (103) as plug (104b) of intermediate pre-hydrolysate solution in the second part of the previous cycle, and illustrated in FIG. 1C. The subsequent cycle can be carried out in a similar manner as described above for the preceding cycle. Such is illustrated in FIG. 2B, where numerals (201), (202), (204a-d), (205a-c) and (206a-d) refer to features similar to the features referred to by numerals (101), (102), (104a-d), (105a-c) and (106a-d) in FIG. 1B.

It is noted that all pre-hydrolysate and hydrolysate solutions in the above examples are suitably aqueous hydrolysate solutions, respectively aqueous pre-hydrolysate solutions.

EXAMPLE 2

Hydrolysis of Woodchips in a Continuous Operation

Experimental Set-Up

In this lab-scale example on a vertical board 7 tubular reactors made of transparent PVC were mounted in a row, the reactors having a height of 0.53 m and a diameter of 0.053 m. Each reactor was equipped with a glass filter plate pore size 0 at the bottom and top (removable at both ends, to allow filling with woodchips and emptying lignin particles). Both bottom and top of each reactor had a liquid tight closure screwed at both ends, said closure having one (central) opening for allowing liquids to be fed to the reactor or liquids to be drained or pumped out of the reactor, with a diameter of 1/16 inch. All reactors were identical.

Storage tanks were present for: fresh 37% hydrochloric acid solution, tridecane displacement fluid, fresh 41-42% HCl solution (cooled to 0° C.). Also present was a tank for receiving a mixture of both used displacement fluid as well as pre-hydrolysate as well as a tank for receiving a mixture of both used displacement fluid as well as hydrolysate. All tanks had an open vent so there was not pressure build up. Linked to each reactor were two 10-port selector valves operated by an electric drive: one with the inlet of selector valve connected to the outlet at the bottom of the reactor, one with the inlet of the selector valve connected to the outlet at the top of the reactor. Between inlet of selector valve and outlet of reactor was a section of transparent tube (material PTFE, diameter about 1/16 inch, length varying for different reactors, at about 10 cm). Mounted onto each tube between reactor outlet (top and bottom) and selector valve was an optical sensor. The sensor was a combination of a yellow LED on one side of a 1/16$^{th}$ inch quartz tube (connected to the PTFE tube) and a light detector on the other side. The electronic output of the sensor was linked via a computer to one of five pumps.

Outlets of the selector valve were connected to the inlets (top and bottom) of the neighboring reactors (two), and with the storage tanks (4). The connecting tube of the outlets was of the same material and diameter as at the inlets.

Five pumps were present: one for pumping in fresh 37% acid at the start (flood filling), one for pumping 37% hydrochloric acid during the process from a storage tank, one for pumping 42% hydrochloric acid from a storage tank, one for displacement fluid to be used in between pre- and main hydrolysis, one for displacement fluid after the main hydrolysis. The pumps were connected to manifolds, both at the top and bottom inlet.

Materials

Chips of rubberwood. Size of woodchips: about 50% had a size of 8-16 mm, about 50% had a size of 16-45 mm. The chips had a moisture content of about 5%. The content of the reactors filled with the woodchips had a bulk density of about 260 kg/m$^3$.
Hydrochloric acid of a concentration of about 37%
Hydrochloric acid of a concentration of 41-42%, as made in-situ by a conventional method.
Tridecane as non-aqueous displacement fluid.

Procedure

At the start of the experiment all reactors were empty, clean, and the hydrochloric acid solutions and displacement fluid were present in sufficient quantities in the storage tanks. Then all reactors were filled with approximately 300 g of wood chips, sieve places and closures put in place and tubing connected.

The system was operated along the scheme as set out in table 1, which states what goes in each reactor and when. Herein, the abbreviations have the following meaning:
R1, R2, . . . R6, R7 as headers of the columns: reactor 1, reactor 2, . . . reactor 6, reactor 7.
In the table:
N no operation
FF flood filling
S stationary
FP1 fresh plug of 37% hydrochloric acid
DF1 displacement fluid to displace 37% hydrochloric acid pre-hydrolysate
FP2 fresh plug of 42% hydrochloric acid
DF2 displacement fluid to displace 42% hydrochloric acid hydrolysate
R1 flow coming from reactor 1 into reactor 2
R2 flow coming from reactor 2 into reactor 3
R3 flow coming from reactor 3 into reactor 4; and so forth
FIN reaction finalized, removing reactor for offloading of lignin.

Each row in this table was planned to last for about 6 hours. For this experiment, for an average amount of biomass of 300 g a theoretical amount of fresh 37% hydrochloric acid and fresh 42% hydrochloric acid required was calculated. The acid was pumped in at a fixed pump speed, for the time required to pump in (about) the calculated amount of acid. When it was determined that the right amount of acid was pumped in, the pump was stopped. Thereafter, displacement fluid (DF1 after FP1, and DF2 after FP2) was pumped into the reactor from the top. The time allowed for DF1 and DF2 being pumped in was 6 hours. As will follow, the sensors at the bottom of each reactor were triggered earlier than that: after about 2-3 hours, by the change from dark coloured (pre)-hydrolysate to clear DF liquid. The sensor tripping caused the pump pumping in DF liquid to stop. The next step was only started after the end of the 6 hour time frame.

The 16 hours pre-hydrolysis was made up of 1 hour flood fill, 2 hours fresh plug into reactor R+1, 6 hours displacement fluid into reactor R+1, 1 hour wait (as R−1 flood fills), 2 hours fresh plug into this reactor, 6 hours displacement in to this reactor. The flow of acids were controlled by timers. Ideally, the pump would be running for the full phase time, as this keeps the flow in the reactors stable and therefore the reaction stable, but that was not achieved yet. The flow of displacement fluid was controlled by optical sensors.

In practice:

Cycle 1 at t=0 hours: for the first reaction cycle reactor 1 was flood-filled from the bottom in about 30 minutes with fresh 37% acid. The system then was idle for 8 hours, as the hydrolysate needed to build up enough color on start up for the required optical sensor colour difference. At the end of this period (t=8 hours) the reactor 2 was flood filled from the bottom with fresh 37% acid.

Reactor 1 was now finished with pre-hydrolysis and DF1, and entered the stage of main hydrolysis. For this, 42% hydrochloric acid (FP2) was added to the bottom of reactor 1 for about 16 hours which drove out the displacement fluid at the top of reactor 1.

The main hydrolysate was in this experiment collected jointly with the displacement fluid that pushed it out (DF2) and collected in one tank initially (after which separation by hand by separation funnel of the two immiscible phases was conducted).

TABLE 1 sequence of activities in reactors 1 to 7.

| R7 | R6 | R5 | R4 | R3 | R2 | R1 | | |
|----|----|----|----|----|----|----|---|---|
| N | N | N | N | N | N | FF | | |
| N | N | N | N | N | N | S | | |
| N | N | N | N | N | FF | S | | |
| N | N | N | N | N | R1 | FP1 | | |
| N | N | N | N | N | R1 | DF1 | | |
| N | N | N | N | FF | S | FP2 | | |
| N | N | N | N | R2 | FP1 | FP2 | | |
| N | N | N | N | R2 | DF1 | FP2 | | |
| N | N | N | FF | S | R1 | FP2 | | |
| N | N | N | R3 | FP1 | R1 | FP2 | | |
| N | N | N | R3 | DF1 | R1 | FP2 | | |
| N | N | FF | S | R2 | R1 | FP2 | | |
| N | N | R4 | FP1 | R2 | R1 | FP2 | | :T |
| N | N | R4 | DF1 | R2 | R1 | DF2 | | B |
| N | FF | S | R3 | R2 | FP2 | FIN | A | |
| N | R5 | FP1 | R3 | R2 | FP2 | FIN | | |
| N | R5 | DF1 | R3 | R2 | DF2 | FIN | | |
| FF | S | R4 | R3 | FP2 | FIN | FIN | | |
| R6 | FP1 | R4 | R3 | FP2 | FIN | FIN | | |
| R6 | DF1 | R4 | R3 | DF2 | FIN | FIN | | |
| S | R5 | R4 | FP2 | FIN | FIN | FIN | | |
| FP1 | R5 | R4 | FP2 | FIN | FIN | FIN | | |
| DF1 | R5 | R4 | DF2 | FIN | FIN | FIN | | |
| R6 | R5 | FP2 | FIN | FIN | FIN | FIN | | |
| R6 | R5 | FP2 | FIN | FIN | FIN | FIN | | |
| R6 | R5 | DF2 | FIN | FIN | FIN | FIN | | |
| R6 | FP2 | FIN | FIN | FIN | FIN | FIN | | |
| R6 | DF2 | FIN | FIN | FIN | FIN | FIN | | |
| FP2 | FIN | FIN | FIN | FIN | FIN | FIN | | |
| DF2 | FIN | FIN | FIN | FIN | FIN | FIN | | |

Thereafter (t=8.5 hours, start cycle 2) fresh hydrochloric acid solution at 37% was fed to the top of reactor 1, pushing out the obtained pre-hydrolysate at the bottom of reactor 1, which was fed to the top of reactor 2. At the bottom outlet of reactor 2 pre hydrolysate was collected. By doing it this way, the reactor stays completely filled with biomass to be hydrolysed and liquid solution, without any headspace or vacuum.

The pre-hydrolysate was collected in a storage tank.
Subsequently (t=16 hours) displacement fluid (DF1) was pumped in at the top of reactor 1, which DF1 pushed out pre-hydrolysate of the bottom of reactor 1. This step was programmed to last 8 hours but the pump was stopped when the sensor at the bottom of R1 sensed the step change from pre-hydrolysate (dark) to displacement fluid (clear due to its immiscibility with HCl/pre-hydrolysate).
Reactor 3 was now flood filled while reactor 2 stayed stationary for 30 mins, after which fresh 37% hydrochloric acid was at the top of reactor 2, followed by displacement fluid DF1.

Moment A in Table 1 (time=T+3 hours) At the outlet at the bottom of reactor R1, the sensor "sensed" a colour change of the flow changing from FP2 (very dark coloured to almost black) to DF2 (clear) and sent a signal to the computer which triggered the pump for DF2 to stop pumping in DF2. After this, reactor R1 was emptied.

Moment B in Table 1 (time=T+2 hours)

At the outlet at the bottom of reactor R4, the sensor "sensed" a colour change of the flow changing from FP1 (very dark coloured to almost black) to DF1 (clear) and sent a signal to stop the pump that pumps in DF1. After this, liquid R3 was pumped in from the bottom and DF1 was released at the top.

Summary Mass Flows In

Table 2 gives the mass flows into the system in this experiment. In reactor 7, during fresh 42% acid flowing in a pump failed.

TABLE 2 mass flows in experiment.

|  |  | R1 | R2 | R3 | R4 | R5 | R6 | R7 |
|---|---|---|---|---|---|---|---|---|
| Biomass in | g | 301.2 | 304.4 | 331.5 | 312.4 | 290.3 | 317.4 | 287.9 |
| Mass 37% acid flood filled | g | 1043 | 842.3 | 847 | 1014.9 | 907 | 1108.8 | 1187.4 |
| 37% fresh acid | g | 373.4 | 397.8 | 385.4 | 255.5 | 384.8 | 384.8 | 409.2 |
| ratio fresh 37%/biomass | g/g | 1.2 | 1.3 | 1.2 | 0.8 | 1.3 | 1.2 | 1.4 |
| DF1 mass | g | 436.1 | 447.4 | 429.7 | 499.6 | 477.1 | 407.5 | 407.5 |
| Pre-hydrolysate to DF1 sensor tripping |  | y | y | y | y | y | y | y |
| DF1 actual time | h | 2.2 | 2 | 2 | 1.3 | 1.8 | 1.5 | 1.5 |
| 42% fresh acid | g | 1947.8 | 500 | 530 | 500 | 535 | 510 | 10* |
| Ratio fresh 42%/biomass | g/g | 6.5 | 1.6 | 1.6 | 1.6 | 1.8 | 1.6 | 0* |
| DF2 mass |  | 815 | 693 | 550 | 672 | 733 | 693 | 448 |
| hydrolysate to DF2 sensor tripping |  | y | y | y | y | y | y | y |
| DF2 actual time | h | 3.3 | 2.8 | 2.7 | 2.8 | 3.0 | 2.8 | 1.8* |
| Mass wet lignin out | g | 494 | 505 | 562 | 541 | 513 | 596 | 599 |
| Mass dry lignin out | g | 79 | 100 | 99 | 103 | 95 | 111 | 155 |
| Retained liquid | g | 416 | 405 | 463 | 438 | 418 | 484 | 444 |
| Hydrolysis mass loss (biomass cf lignin) | yield (wt %) | 26% | 33% | 30% | 33% | 33% | 35% | 54% |
| Theoretical lignin | g | 70.8 | 71.5 | 77.9 | 73.4 | 68.2 | 74.6 | 67.6 |
| Theoretical hydrolysis efficiency | % | 97% | 88% | 92% | 88% | 88% | 85% | 60% |

*pump failed.

Sensor Activity

Results

Part of the results, e.g. on the lignin and efficiency of hydrolysis are given in table 2. Further results on the hydrolysates are in table 3. Although for lignin the amount per reactor was measured, the liquid hydrolysates of the various reactors were jointly collected (hydrolysate and pre-hydrolysate separate). Hydrolysates were, prior to analysis on monomers, subjected to a second hydrolysis, which hydrolysed oligomers obtained in each of the pre- and main hydrolysate.

TABLE 3 analysis of hydrolysates obtained

|  | Glucose yield (wt %) | Xylose + mannose yield (wt %) | Glucose purity of product |
|---|---|---|---|
| Pre-hydrolysate | 5% | 42% | 22% |
| Main hydrolysate | 37% | 34% | 73% |
| Lost (by difference) | 58% | 24% |  |

As to the amount referred to as "lost" in table 3: this relates to hydrolysed sugars which are still present in the liquid which is retained in the lignin particles that are obtained from the reactors (the lignin chips are still wet) we well as any potential (hemi-)cellulose which was not hydrolysed.

Conclusion

When ligno-cellulosic biomass (in the form of wood chips) was subjected to the process of the current invention in this experiment, it yielded two products: an aqueous pre-hydrolysate rich in xylose and mannose (and their oligomers) and an aqueous hydrolysate rich in glucose (and oligomers), next to lignin.

Additionally it was shown that this process can be operated in a continuous way, in the sense that one reactor was emptied of lignin (and could be filled with fresh wood chips) whilst the other reactors continued to operate, whilst also a minimum of pumps and storage tanks is needed.

The use of a non-aqueous displacement liquid secured separation of hydrolysate of hemicellulose and hydrolysate of cellulose to a large extent and contributed to steady state as well as providing a driving force for sequential reactions. Simultaneously, it also facilitated control of the various reactions without the danger of diluting the acids needed for the hydrolysis steps.

Still further, the sensors at the bottom of each reactor being triggered earlier than the allowed 6 hours (after about 2-3 hours) by the change from dark coloured (pre-)hydrolysate to clear DF liquids passing the sensor showed process control in the claimed process was possible with non-invasive sensors.

The invention claimed is:

1. A process for the conversion of a solid material containing hemicellulose, cellulose and lignin, wherein the process comprises the following steps:
 (i) hydrolyzing, at a temperature equal to or less than 40° C., at least part of the hemicellulose of the solid material by contacting the solid material with a first aqueous hydrochloric acid solution, wherein the first aqueous hydrochloric acid solution has a hydrochloric acid concentration in the range from equal to or more than 15.0 wt. % to less than 40.0 wt. %, based on the weight amount of water and hydrochloric acid in the first aqueous hydrochloric acid solution, yielding a remaining solid material and an aqueous first hydrolysate product solution;

(ii) displacing the aqueous first hydrolysate product solution from the remaining solid material with a non-aqueous displacement fluid;

(iii) hydrolyzing, at a temperature equal to or less than 40° C. at least part of the cellulose of the remaining solid material by replacing the non-aqueous displacement fluid with a second aqueous hydrochloric acid solution, wherein the second aqueous hydrochloric acid solution has a hydrochloric acid concentration in the range from equal to or more than 40.0 wt. % to equal to or less than 51.0 wt. %, based on the weight amount of water and hydrochloric acid in the second aqueous hydrochloric acid solution, yielding a residue and an aqueous second hydrolysate product solution, wherein the process is carried out in one or more reactors and wherein the one or more reactors comprise a cylindrical vessel, and wherein said non-aqueous displacement fluid comprises an inert gas or inert, hydrophobic liquid having a density equal to or less than 1000 kilograms per cubic meter ($kq/m^3$), and wherein the non-aqueous displacement fluid is supplied to the one or more reactors in a downward fashion.

2. The process according to claim 1, wherein the non-aqueous displacement fluid in step (iii) is removed from a top of the one or more reactors by pumping the second aqueous hydrochloric acid solution into the one or more reactors from the bottom.

3. The process according to claim 1, wherein after the non-aqueous displacement fluid supplied from a top of the one or more reactors in step (ii) has reached the bottom of the one or more reactors, supplying the non-aqueous displacement fluid in step (ii) is stopped and the pumping in of the second aqueous hydrochloric acid solution is started.

4. The process according to claim 1, further comprising an additional step (iv) comprising displacing the aqueous second hydrolysate product solution from the residue with additional non-aqueous displacement fluid.

5. The process according to claim 1, wherein the non-aqueous displacement fluid has a boiling temperature at 0.1 MegaPascal of equal to or more than 80° C.

6. The process according to claim 1, wherein the non-aqueous displacement fluid has a viscosity at 20° C. of equal to or less than 5 centipoise (cP).

7. The process according to claim 1, wherein the non-aqueous displacement fluid comprises or consists of one or more alkanes chosen from the group consisting of cyclic hexane, normal hexane, iso-hexane and other hexanes, normal heptane, iso-heptane and other heptanes, normal octane, iso-octane and other octanes, normal nonane, iso-nonane and other nonanes, normal decane, iso-decane and other decanes, normal undecane, iso-undecane and other undecanes, normal dodecane, iso-dodecane and other dodecanes, normal tridecane, iso-tridecane and other tridecanes, normal tetradecane, iso-tetradecane and other tetradecanes, normal pentadecane, iso-pentadecane and other pentadecanes, normal hexadecane, iso-hexadecane and other hexadecanes.

8. The process according to claim 1, wherein the non-aqueous displacement fluid is retrieved from step (iii), optionally stored in a displacement fluid storage vessel, and recycled to step (ii).

9. The process according to claim 1, wherein the process is carried out in a plurality of reactors, connected in series, comprising in the range from equal to or more than 2 to equal to or less than 16 reactors.

10. The process according to claim 1,
wherein the solid material containing hemicellulose, cellulose, and lignin is residing in a stationary phase within the one or more reactors and wherein the solid material containing hemicellulose, cellulose, and lignin is contacted with a mobile phase that moves through the one or more reactors, the mobile phase includes:

a zone comprising one or more portions of the first aqueous hydrochloric acid solution;

a zone comprising one or more portions of a liquid non-aqueous displacement fluid; and a zone comprising one or more portions of the second aqueous hydrochloric acid solution.

11. The process according to claim 1, wherein the solid material containing hemicellulose, cellulose and lignin is residing in a stationary phase within a vertical reactor, and is contacted in step (i) with one or more zones of a mobile phase that moves through the one or more reactors, including a zone comprising one or more portions of the first aqueous hydrochloric acid solution, to yield the aqueous first hydrolysate product solution and the remaining solid material; and the aqueous first hydrolysate product solution is subsequently displaced from the remaining solid material with a non-aqueous displacement fluid, by contacting the remaining solid material in step (ii) with a subsequent zone of the mobile phase that moves through the one or more reactors in a downward fashion, wherein the subsequent zone comprises one or more portions of a liquid non-aqueous displacement fluid; and the liquid non-aqueous displacement fluid is subsequently displaced from the remaining solid material with the second aqueous hydrochloric acid solution, by contacting the remaining solid material in step (iii) with one or more subsequent zones of the mobile phase that moves through the one or more reactors, including a zone comprising one or more portions of the second aqueous hydrochloric acid solution, to yield the aqueous second hydrolysate product solution and the residue; and optionally the aqueous second hydrolysate product solution is subsequently displaced from the residue with additional non-aqueous displacement fluid, by contacting the residue in an optional step (iv) with a subsequent zone of the mobile phase that moves through the one or more reactors in a downward fashion, wherein the subsequent zone comprises one or more further portions of the additional non-aqueous displacement fluid.

12. The process according to claim 1, wherein the process is carried out in a reactor sequence of two or more reactors, wherein during steps (i), (ii) and (iii) the solid material containing hemicellulose, cellulose, and lignin is residing stationary within each reactor, whilst the first aqueous hydrochloric acid solution and/or the non-aqueous displacement fluid and/or the second aqueous hydrochloric acid solution is/are passed, from one reactor into another reactor.

13. A process for the conversion of a solid material containing hemicellulose, cellulose and lignin, wherein the process comprises the following steps:

(i) hydrolyzing, at a temperature equal to or less than 40° C. at least part of the hemicellulose of the solid material by contacting the solid material with a first aqueous hydrochloric acid solution, wherein the first aqueous hydrochloric acid solution has a hydrochloric acid concentration in the range from equal to or more than 15.0 wt. % to less than 40.0 wt. %, based on the weight amount of water and hydrochloric acid in the first aqueous hydrochloric acid solution, yielding a remaining solid material and an aqueous first hydrolysate product solution;

(ii) displacing the aqueous first hydrolysate product solution from the remaining solid material with a non-aqueous displacement fluid;

(iii) hydrolyzing, at a temperature equal to or less than 40° C. at least part of the cellulose of the remaining solid material by replacing the non-aqueous displacement fluid with a second aqueous hydrochloric acid solution, wherein the second aqueous hydrochloric acid solution has a hydrochloric acid concentration in the range from equal to or more than 40.0 wt. % to equal to or less than 51.0 wt. %, based on the weight amount of water and hydrochloric acid in the second aqueous hydrochloric acid solution, yielding a residue and an aqueous second hydrolysate product solution, wherein process step (i) is carried out in at least one reactor of cylindrical shape, and wherein said non-aqueous displacement fluid comprises an inert gas or an inert, hydrophobic liquid having a density equal to or less than 1000 kilograms per cubic meter ($kg/m^3$), and wherein the non-aqueous displacement fluid is supplied to the reactor at the top of said one or more reactors, pushing out said aqueous first hydrolysate product solution at the bottom from said one or more reactors.

14. The process according to claim 13, wherein said non-aqueous displacement fluid is supplied at the top of said one or more reactors until said non-aqueous displacement fluid exits the bottom of the one or more reactors, at or after which moment the supply of non-aqueous displacement fluid at the top of said one or more reactors is stopped and subsequently or simultaneously the second aqueous hydrochloric acid solution is supplied at the bottom of said one or more reactors thereby reversing the flow of non-aqueous displacement fluid in an upward fashion and pushing out the non-aqueous displacement fluid at the top of the one or more reactors.

* * * * *